US 7,635,359 B2

(12) United States Patent
Nakazawa et al.

(10) Patent No.: US 7,635,359 B2
(45) Date of Patent: Dec. 22, 2009

(54) RECEPTACLE FOR USE WITH A MEDICAL SUCTION DEVICE

(75) Inventors: Hajime Nakazawa, Kishiwada (JP); Hiroaki Takimoto, Hannan (JP)

(73) Assignee: Daiken Iki Kabushiki Kaisha (JP)

( * ) Notice: Subject to any disclaimer, the term of this patent is extended or adjusted under 35 U.S.C. 154(b) by 519 days.

(21) Appl. No.: 10/559,700

(22) PCT Filed: Jun. 8, 2004

(86) PCT No.: PCT/JP2004/008271

§ 371 (c)(1),
(2), (4) Date: Dec. 6, 2005

(87) PCT Pub. No.: WO2004/110522

PCT Pub. Date: Dec. 23, 2004

(65) Prior Publication Data

US 2006/0276762 A1 Dec. 7, 2006

(30) Foreign Application Priority Data

Jun. 10, 2003 (JP) ............................. 2003-165277

(51) Int. Cl.
*A61M 1/00* (2006.01)
*A61M 31/00* (2006.01)
*A61M 37/00* (2006.01)
*A61M 5/14* (2006.01)
*B65B 1/04* (2006.01)
*B65B 3/04* (2006.01)
*B65B 3/00* (2006.01)

(52) U.S. Cl. ............................ 604/319; 604/27; 604/48; 604/73; 604/93.01; 604/129; 604/131; 604/256; 604/540; 604/320; 604/321; 141/98; 141/129; 141/313

(58) Field of Classification Search ................... 604/82, 604/85, 87, 88, 89, 93.01, 319, 322, 327, 604/328; 141/98, 114, 313, 318, 346, 363, 141/382, 383
See application file for complete search history.

(56) References Cited

U.S. PATENT DOCUMENTS 2,999,500 A * 9/1961 Schurer ....................... 604/322
3,648,698 A * 3/1972 Doherty ....................... 604/319
3,767,078 A * 10/1973 Gortz et al. ..................... 222/95
3,945,392 A * 3/1976 Deaton et al. ................ 137/205
3,946,739 A * 3/1976 Berman et al. .............. 604/128

(Continued)

FOREIGN PATENT DOCUMENTS

| JP | 9-56810 | 3/1997 |
| WO | WO 01/49344 A1 | 7/2001 |
| WO | WO-149344 A1 * | 7/2001 |

*Primary Examiner*—Leslie R Deak
*Assistant Examiner*—Adam Marcetich
(74) *Attorney, Agent, or Firm*—Gerald E. Hespos; Anthony J. Casella

(57) ABSTRACT

Disclosed is a receptacle for use with a medical suction device which is equipped with a cover body and an external case for detachably holding and air-tightly surrounding the receptacle and a patient-side tube for introducing waste liquid into the receptacle, and designed to create a negative pressure in both an interior space of the cover body and the external case and an interior space of the receptacle so as to allow waste liquid to be sucked into the receptacle through the patient-side tube. The receptacle has an air-pervious/liquid-impervious element having air perviousness and liquid imperviousness. The air-pervious/liquid-impervious element at least partly constitutes a portion of the receptacle to be surrounded by the cover body and the external case.

14 Claims, 16 Drawing Sheets

U.S. PATENT DOCUMENTS

| | | | |
|---|---|---|---|
| 4,058,123 A * | 11/1977 | May | 604/30 |
| 4,111,204 A * | 9/1978 | Hessel | 604/321 |
| 4,187,860 A * | 2/1980 | Villari | 600/576 |
| 4,379,455 A * | 4/1983 | Deaton | 604/320 |
| 4,397,643 A * | 8/1983 | Rygiel | 604/317 |
| 4,466,888 A * | 8/1984 | Verkaart | 210/232 |
| 4,500,308 A * | 2/1985 | Kurtz et al. | 604/6.15 |
| 4,516,973 A * | 5/1985 | Telang | 604/319 |
| 5,275,585 A * | 1/1994 | Olson | 604/319 |
| 5,306,264 A * | 4/1994 | Ferguson et al. | 604/333 |
| 5,669,892 A * | 9/1997 | Keogh et al. | 604/320 |
| 6,077,233 A * | 6/2000 | Blake, III | 600/573 |
| 6,364,864 B1 * | 4/2002 | Mohiuddin et al. | 604/410 |
| 6,506,184 B1 * | 1/2003 | Villefrance | 604/333 |
| 2002/0029021 A1 * | 3/2002 | Bormann et al. | 604/252 |
| 2002/0138066 A1 * | 9/2002 | Manica et al. | 604/410 |
| 2003/0014022 A1 * | 1/2003 | Lockwood et al. | 604/315 |
| 2004/0078023 A1 * | 4/2004 | Gollier et al. | 604/410 |

* cited by examiner

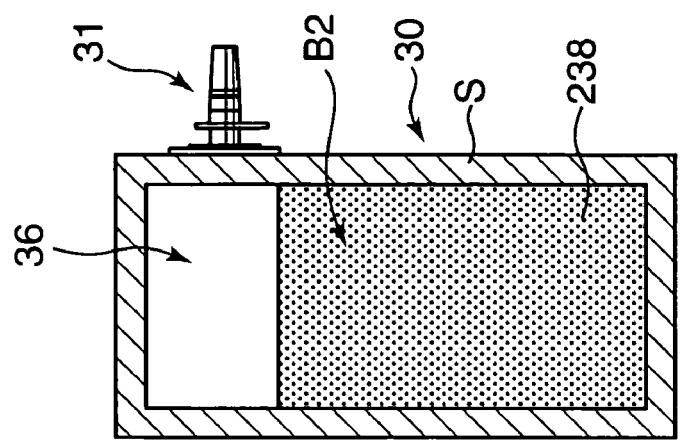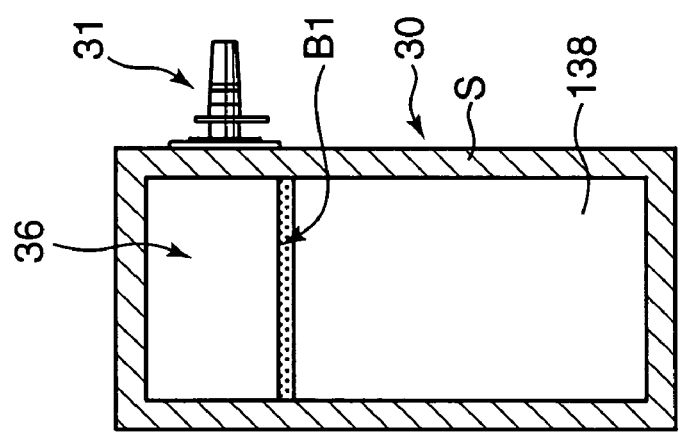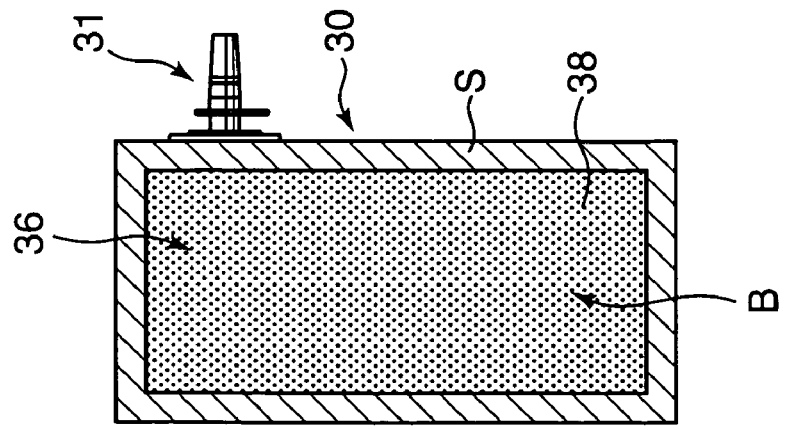

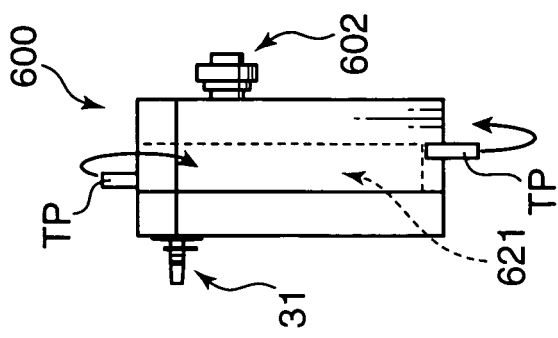
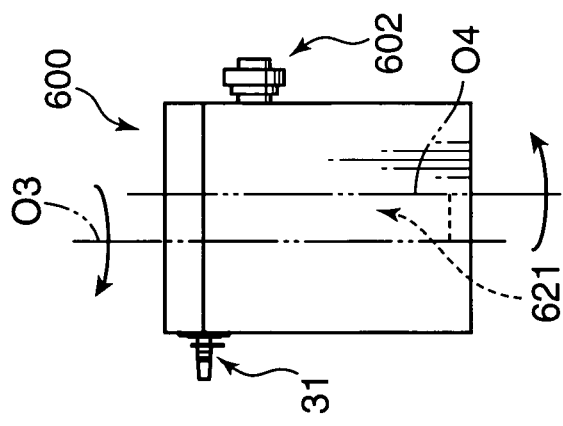
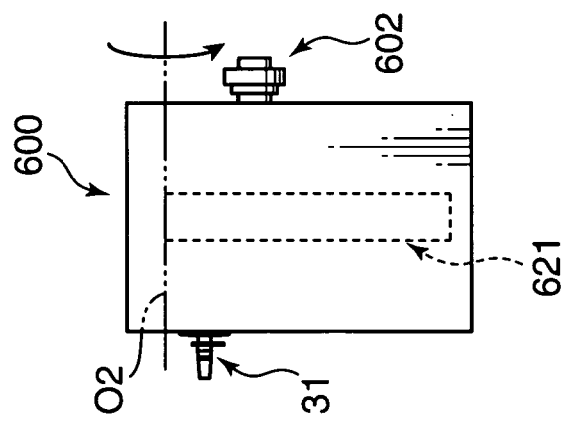
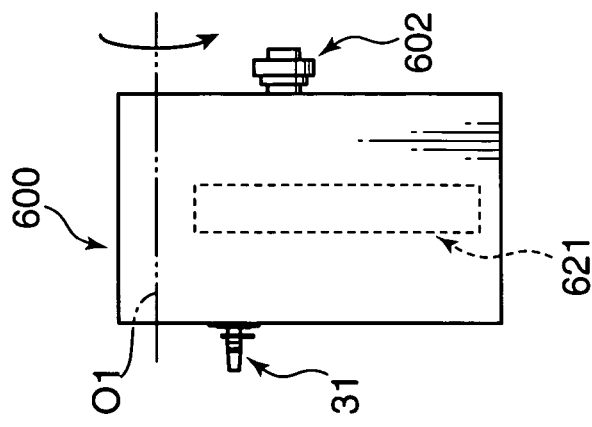

RECEPTACLE FOR USE WITH A MEDICAL SUCTION DEVICE

BACKGROUND OF THE INVENTION

1. Field of the Invention

The present invention relates to a medical suction device equipped with a rigid case, a receptacle adapted to be at least partly surrounded by the rigid case in an airtight manner, and a patient-side tube for introducing waste liquid into the receptacle, and designed to create a negative pressure in both an interior space of the rigid case and an interior space of the receptacle so as to allow waste liquid to be sucked into the receptacle through the suction tube.

2. Description of the Related Art

Generally, waste liquid generated during surgery or therapy, such as blood or rinse saline, is dealt with through an operation of sucking and collecting waste liquid in a receptacle bag, and discarding the receptacle bag after the surgery or therapy. This type of operation is carried out using a liquid suction device as disclosed, for example, in Japanese Patent Laid-Open Publication No. 8-112344 (hereinafter referred to as "prior art document").

This liquid suction device comprises a flexible receptacle bag, and a rigid case for housing the receptacle bag, and a member for, in the state after the receptacle bag is housed in the rigid case, preventing gas communication between a space located inside the rigid case and outside the receptacle bag (hereinafter referred to as "out-of-bag interior space of the rigid case") and an interior space of the receptacle bag, and preventing gas communication between the out-of-bag interior space of the rigid case and an exterior space of the rigid case. A suction-side tube for discharging an air in the interior space of the receptacle bag and an air in the out-of-bag interior space of the rigid case individually (i.e., for creating a negative pressure in the respective spaces individually), and a patient-side tube for introducing waste liquid into the interior space of the receptacle bag, are fluidically connected to the receptacle bag of the liquid suction device in such a manner as to maintain the above gas-communication states. Further, a member for stopping the suction of waste liquid at a time when a desired volume of waste liquid is introduced into the receptacle bag (i.e., for stopping creating a negative pressure in the respective spaces) is interposed in the suction-side tube.

The liquid suction device disclosed in the prior art document is designed to create a negative pressure simultaneously in the interior space of the receptacle bag and the out-of-bag interior space of the rigid case so as to allow the respective spaces to have an approximately even pressure. This makes it possible to collect waste liquid in the receptacle bag through the patient-side tube while suppressing compression of the flexible receptacle bag. In an operation for disposal of the collected waste liquid, the suction-side tube is detached from the receptacle bag, and the receptacle bag is detached from the rigid case. Then, the receptacle bag and the patient-side tube will be collectively discarded.

However, in the liquid suction device, before the use, each of the suction-side tube and the patient-side tube has to be attached to the receptacle bag. Thus, the preparatory operation for the liquid suction device inevitably becomes complicated. This means an increase in time period required for the preparatory operation. In addition, the need for connecting the plural tubes becomes a factor causing an error in selecting a connection portion corresponding to each of the tubes or an improper connection.

Moreover, in an operation for disposal of the collected waste liquid, the suction-side tube has to be detached from the receptacle bag. Thus, the disposal operation also becomes complicated. This means an increase in time period required for disposing of the receptacle bag, and leads to an increase in the frequency of contact of a medical staff with the suction-side tube through which patient's blood or bodily fluid is likely to attach to the medical staff. This situation is undesirable from the aspect of prevention of secondary infections.

Further, many of conventional liquid suction devices are a type in which the receptacle bag can be detached from the rigid case only after detaching both the suction-side and patient-side tubes. In the use of this type of liquid suction device, a disposal operation becomes more complicated.

In view of the above problems, it is therefore an object of the present invention to provide a receptacle and a medical suction device equipped with the receptacle, capable of achieving enhanced efficiency of preparatory and disposal operations, and maximally preventing a secondary infection and an improper connection of tubes.

SUMMARY OF THE INVENTION

According to an aspect of the present invention, a receptacle is used with a medical suction device which is equipped with a rigid case for detachably holding and air-tightly surrounding at least a portion of the receptacle, and a patient-side tube for introducing waste liquid into the receptacle, and designed to create a negative pressure in both an interior space of the rigid case and an interior space of the receptacle so as to allow waste liquid to be sucked into the receptacle through the patient-side tube. The receptacle comprises an air-pervious/liquid-impervious element having air perviousness and liquid imperviousness. The air-pervious/liquid-impervious element at least partly constitutes at least the portion of the receptacle to be surrounded by the rigid case. Further, the air-pervious/liquid-impervious element is adapted to discharge an air in the interior space of the receptacle to the interior space of the rigid case in response to the negative pressure created in the interior space of the rigid case.

These and other objects, features, aspects, and advantages of the present invention will become more apparent from the following detailed description of the preferred embodiments/examples with reference to the accompanying drawings.

BRIEF DESCRIPTION OF THE DRAWINGS

FIGS. 5A to 5C are front views showing a receptacle in the medical suction device in FIG. 1, wherein FIGS. 5A, 5B and 5C show, respectively, an air-pervious portion formed in the entire surface of the receptacle, an air-pervious portion formed in the receptacle at a position corresponding a target liquid level, and an air-pervious portion formed in the receptacle in the entire area extending downward from the target liquid level.

FIGS. 6A and 6B show a partition portion formed in a receptacle according to anther embodiment of the present invention, wherein FIG. 6A is a front view of the receptacle, and FIG. 6B is a top plan view of the receptacle clamped by a clamp member.

FIGS. 10A to 10D are top plan views showing a procedure for folding the receptacle illustrated in FIG. 7.

DETAILED DESCRIPTION OF THE PREFERRED EMBODIMENTS

With reference to the drawings, a preferred embodiment of the present invention will now be described.

Figure 1:
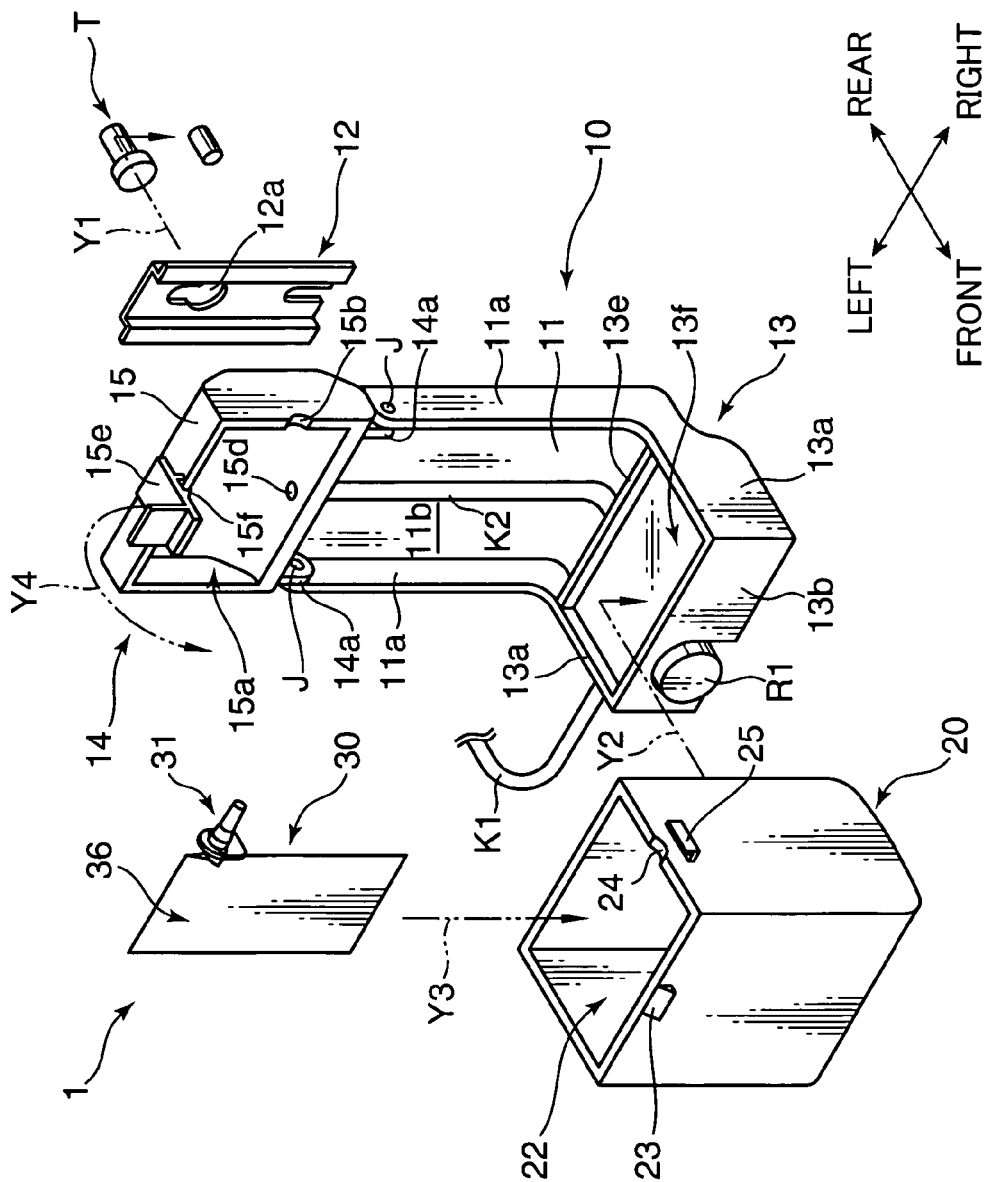
FIG. 1 is an exploded perspective view showing the structure of a medical suction device according to one embodiment of the present invention.
Figure 2:
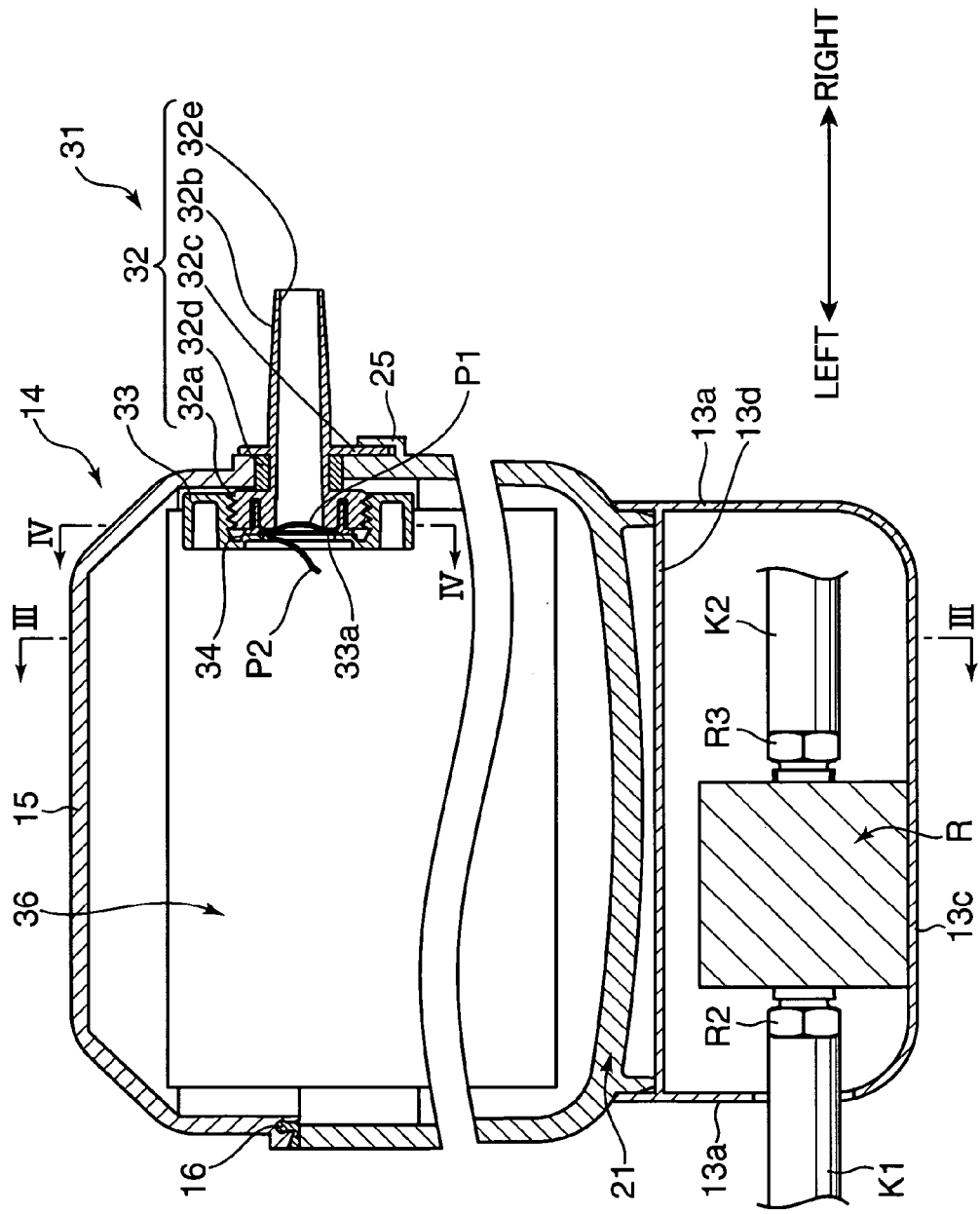
FIG. 2 is a sectional front view showing the medical suction device in FIG. 1, which is set up in a usable state.
Figure 3:
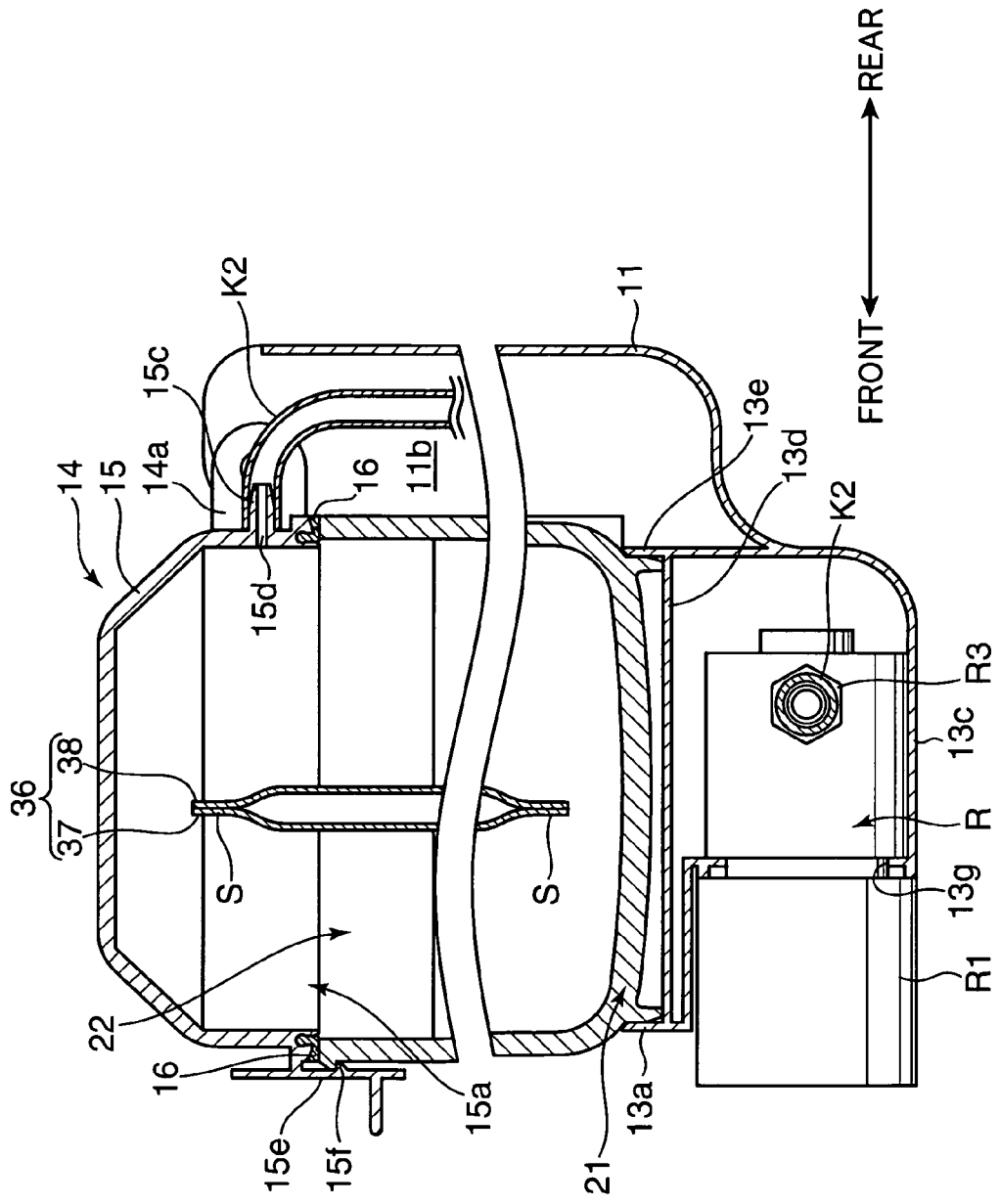
FIG. 3 is a sectional view of the medical suction device, taken along the line III-III in FIG. 2.

FIG. 1 is an exploded perspective view showing the structure of a medical suction device according to one embodiment of the present invention. FIG. 2 is a sectional front view showing the medical suction device in FIG. 1, which is set up in a usable state, and FIG. 3 is a sectional view of the medical suction device, taken along the line III-III in FIG. 2.

Referring to these figures, the medical suction device 1 comprises a holder 10 adapted to be hung on a mounting pin T fixed onto a wall surface of a medical facility, such as a medical center, an external case 20 adapted to be detachably attached to the holder 10, and a receptacle 30 adapted to be housed in the external case 20.

The holder 10 includes a holder base 11 formed to have an approximately rectangular plate shape extending vertically. A bracket 12 having a bracket hole 12a engageable with the mounting pin T is fixed onto one of opposite surfaces of the holder base 11. The following description will be made on the assumption that a direction in which the surface of the holder base 11 having the bracket 13 fixed thereonto faces is rearward, and a width direction of the holder base 11 is a rightward/leftward or lateral direction.

A pair of standing walls 1a is formed, respectively, along opposite lateral edges of the holder base 11 to protrude frontward. A groove 11b is formed on the frontward side of the holder base 11 by the pair of standing walls 11a. The groove 11b has a frontward-facing opening and extends vertically. The holder base includes a mounting/housing portion 13 which is formed at a lower end thereof to extend frontward, and adapted to mount the external case 20 thereon and house an after-mentioned regulator R therein.

Specifically, the mounting/housing portion 13 comprises a pair of right and left lateral plates 13a each extending frontward from a corresponding one of the standing walls 11a, a front plate 13b extending between the lateral plates 13a, a housing bottom plate 13c fixed to respective lower edges of the front plate 13b and the lateral plates 13a, and a top plate 13d disposed in opposed relation to the housing bottom plate 13c. This top plate 13d is attached to the lateral plates 13a and the front plate 13b at a position slightly below respective upper edges thereof. Further, a positioning plate 13e is attached along a rear edge of a top surface of the top plate 13d to extend upward. Thus, a mounting hole 13f having an upward-facing opening is formed by the positioning plate 13e, the lateral plates 13a and the front plate 13b of the mounting/storage portion 13. When an lower end portion of the external case 20 is fitted into the mounting hole 13f, the external case 20 is positioned relative to the frontward/rearward and rightward/leftward directions. A regulator R is housed in a space defined by the lateral plates 13a, the front plate 13b, the housing bottom plate 13c and the top plate 13d.

The regulator R includes a dial R1 extending frontward. This dial R1 penetrates through an insertion hole 13g formed in the front plate 13b, and protrudes from a front surface of the mounting/housing portion 13. In this embodiment, the regulator R further includes a pair of left and right nipples R2, R3. The left nipple R2 is fluidically connected to a suction source (not shown) installed in a medical facility, through a suction-side tube K1, and the right nipple R3 is fluidically connected to a proximal end of a suction-side tube K2. A valve may be interposed between the suction source and the suction-side tube K1 to switchingly turn on/off the supply of a negative pressure to the suction-side tube K1.

The suction-side tube K2 extends rearward from the nipple R3. Then, an intermediate portion of the suction-side tube K2 extends through the groove 11b of the holder base 11, and an distal end of the suction-side tube K2 is fluidically connected to an external cover 14. While the suction-side tube K2 is arranged to extend through the groove 11b, the holder base 11 may be designed to form a groove having a rearward-facing opening and extending vertically, and the intermediate portion of the suction-side tube K2 may be arranged to extend along this groove. In this case, even after the external case 20 is detached from the holder base 11, the suction-side tube K2 can be invisibly hided to provide enhanced appearance.

The external cover 14 includes a pair of right and left swingable members 14a each of which is formed at a base end thereof and pivoted onto an inner surface of a corresponding one of the standing walls 11a. These swingable members 14a are attached to the corresponding standing walls 11a in a swingable manner about a pair of axes J each extending laterally. The external cover 14 includes a cover body 15 formed at respective distal ends of the swingable members 14a.

The cover body 15 is an approximately-rectangular-shaped bottomed case having an opening 15a. The cover body 15 has a cutout portion 15b formed in a right edge of a surface having the opening 15a. Further, the cover body 15 has a nipple portion 15c formed in a surface on the side of the base end thereof to allow the suction-side tube K2 to be fitted thereonto, and the nipple portion 15c is formed with a communication hole 15d in fluid communication with an interior space of the cover body 15. The cover body 15 also has a tongue portion 15e formed on a side surface of the distal end thereof to extend beyond the surface having the opening 15a, and the tongue portion 15e has an inner surface (a surface on the side of the axes J) formed with an engagement pawl 15f engageable with the external case 20. A sealing member 16 is attached along a peripheral edge of the surface formed with the opening 15a to ensure airtightness relative to a top surface of the external case 20.

The external case 20 is formed as an approximately rectangular-shaped case which includes a bottom portion 21 adapted to be fitted into the mounting hole 13f, and an opening 22 facing upward in the state after the bottom portion 21 is fitted into the mounting hole 13f. The external case 20 is provided with an engagement pawl 23 which is formed on an upper edge of a front surface to extend frontward, and adapted to be engaged with the engagement pawl 15f of the cover body 15 in such a manner as to prevent the engagement pawl 5f from disengaging from the engagement pawl 23 in the vertical direction. The external case has a cutout portion 24 formed in a right edge of a surface having the opening 22 to clamp a port portion 31 of the receptacle 30 in cooperation with the cutout portion 15b of the cover body 15. While each of the cutout portions 15b, 24 is formed on only the right side, each of the cutout portions 15b, 24 may be formed in both the right and left sides. In this case, it is necessary to allow a blank cap or the like to be clamped between one pair of cutout portions 15b, 24 which are not used for clamping the port portion 31.

Further, the external case 20 has a hook-shaped positioning portion 25 formed on a right surface thereof to prevent a lateral movement of the port portion 31, and an after-mentioned positioning member 32c is inserted between the positioning portion 25 and an outer surface of the external case 20.

The receptacle 30 comprises the port portion 31 adapted to allow a patient-side tube (not shown) for sucking waste liquid therethrough to be fitted thereonto, and a receptacle body 36 for receiving the sucked waste liquid therein.

The port portion 31 include a connection adapter 32 having an externally threaded portion 32a at a left end thereof, a joining adapter 33 threadingly engaged with the externally threaded portion 32a, and a check valve 34 clamped between the connection adapter 32 and the joining adaptor 33.

The connection adaptor 32 has a nipple portion 32b adapted to be fluidically connected with the patient-side tube, a positioning member 32c adapted to be engaged with the positioning portion 25, a clamped portion 32d adapted to be clamped between the cutout portions 15b, 24, and a guide hole 32e for guiding waste liquid toward the receptacle body 36.

The clamped portion 32d has an outer peripheral surface made of a synthetic resin having elasticity. That is, the clamped portion 32d is designed to provide airtightness between the clamped portion 32d and the cover body 15/the external case 20, in a circumferential direction of the outer peripheral surface of the clamped portion 32d when the clamp potion 32b is clamped between the cutout portion 15b of the cover body 15 and the cutout portion 24 of the external case 20.

The joining adaptor 33 is formed approximately concentrically to the guide hole 32e, and formed with an introducing hole 33a capable of introducing waste liquid toward the receptacle body 36.

The check valve 34 is made of a synthetic resin having elasticity, and clamped between respective portions of the connection adaptor 32 and the joining adaptor 33 in the vicinity of peripheries of the guide-hole 32a and the introducing hole 33a. The check valve 34 has a sealing tongue 34a (see FIG. 4) formed to be cantilevered relative to its peripheral portion clamped in the above manner. This sealing tongue 34a is designed to be swingably moved between a position P1 where it closes the guide hole 32e of the connection adaptor 32 and a position P2 where it opens the guide hole 32e. That is, the check valve 34 is designed to allow waste liquid to flow in a direction from the connection adaptor 32 toward the receptacle body 36, and prevent waste liquid from flowing in a direction from the receptacle body 36 toward the connection adaptor 32, while providing liquid-tightness between the connection adaptor 32 and the joining adaptor 33.

While the connection adaptor 32 in the port portion 31 is designed to be detachable relative to the joining adaptor 33, the present invention is not limited to this structure, but the connection adaptor 32 and the joining adaptor 33 may be integrally formed as a single component, and the periphery of the check valve 34 may be fixed onto a left end surface of the obtained integral component by means of adhesive bonding or the like.

In other words, this port portion 31 is intended to detach the connection adaptor 32 from the joining adaptor 33 when it becomes necessary to intentionally discharge a waste liquid collected in the receptacle body 36 outside, so as to allow the collected waste liquid to be discharged. Thus, if this discharge function is unnecessary, the connection adaptor 32 and the joining adaptor 33 may be integrally formed as a single component.

Figure 4:
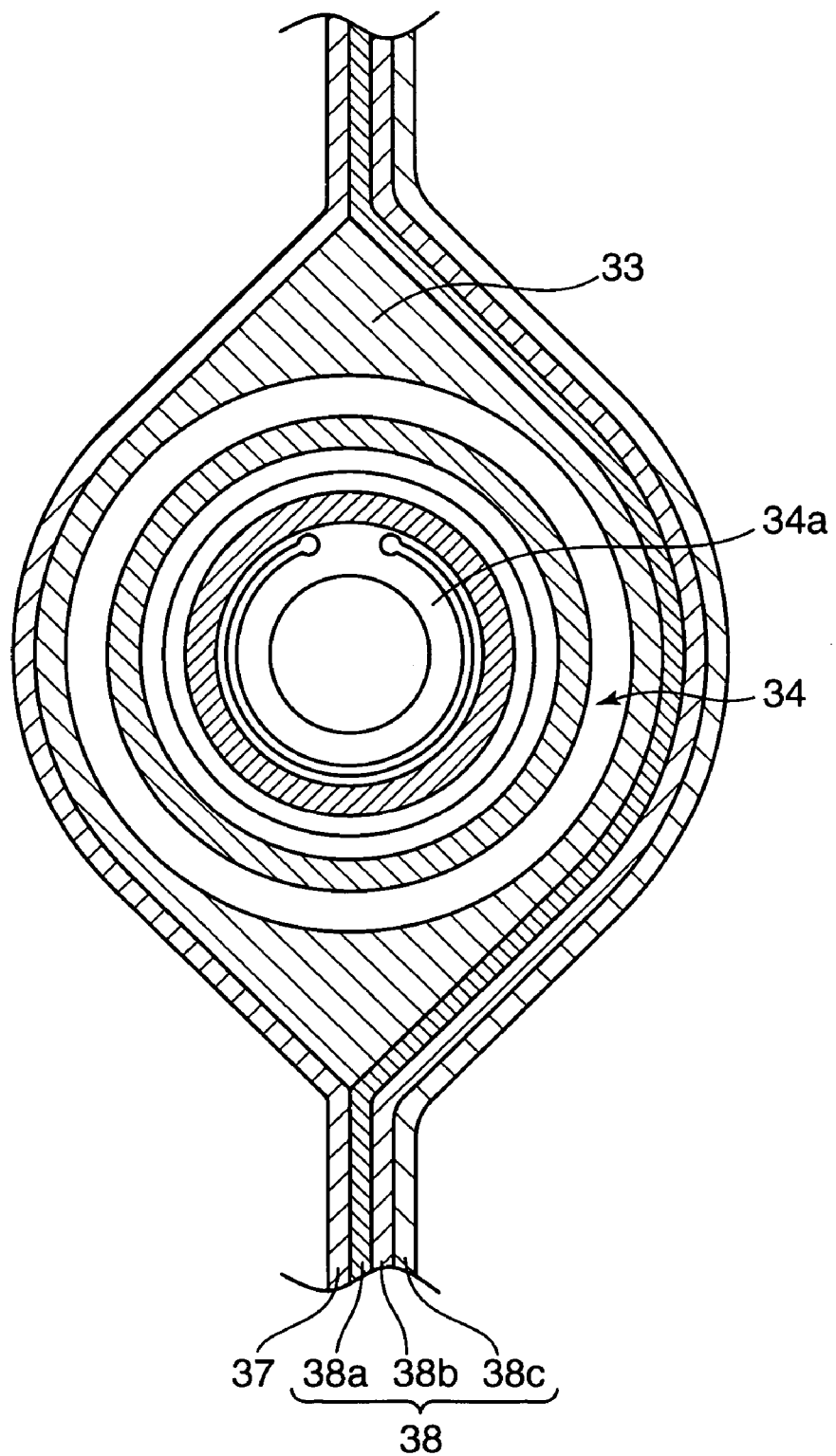
FIG. 4 is a sectional view of the medical suction device, taken along the line IV-IV in FIG. 2.

As shown in FIGS. 4 and 5A, the receptacle body 36 comprises a sheet 37 having air-imperviousness and liquid-imperviousness, and an air-pervious sheet 38 having air-perviousness and liquid-imperviousness. Respective peripheral edges S of the sheet 37 and the air-pervious sheet 38 are joined together by means of fusion bonding or the like, and the joining adaptor 33 is joined between the sheet 37 and the air-pervious sheet 38 in a portion of the peripheral edges S.

In this embodiment, the sheet 37 is made of polyethylene resin. The air-pervious sheet 38 includes a joining layer 38a joined to the sheet 37, an intermediate layer 38b bonded to the joining layer 38a, and an outer layer 38c joined to the intermediate layer 38b by means of fusion bonding or adhesive bonding.

The joining layer 38a is made of one selected from materials having air-perviousness and capability to ensure a bonding force relative to the sheet 37, for example, a porous polyethylene sheet having a plurality of pores penetrating in a thickness direction thereof.

The intermediate layer 38b is made of one selected from materials having air-perviousness, liquid-imperviousness, and capability to ensure a bonding force relative to the joining layer 38a and the outer layer 38c, for example, micro-porous polypropylene with a structure having micro-pores penetrating in a thickness direction thereof and complicated through-channels of the micro-pores.

The outer layer 38c is made of one selected from materials having air-perviousness and capability to ensure a bonding force relative to the intermediate layer 38b, for example, commonly used nonwoven fabric.

The structure of the medical suction device 1 is organized below. The combination of the cover body 15 and the external case 20 corresponds to one example of a rigid case, and the receptacle 30 corresponds to one example of a receptacle. The opening 22 of the external case 20 corresponds to one example of an upward-facing opening, and the sheet 37 corresponds to one example of a first sheet. The air-pervious sheet 38 corresponds to an air-pervious/liquid-impervious element and a second sheet.

Returning to FIGS. 1 to 3, when the medical suction device 1 is used, the holder 10 is firstly hung on the mounting pin T, as indicated by the arrow Y1, and fixed, for example, onto a wall surface of a medical facility. Then, after the suction-side tube K1 fluidically connected to the regulator R is fluidically connected to the suction source (not shown), the external case 20 is attached to the holder 10, as indicated by the arrow Y2, and the receptacle 30 is set up in the external case 20, as indicated by the arrow Y3. In this state, when the cover body 15 is swung or rotated, as indicated by the arrow Y4, to close the opening 22 of the external case 20 by the cover body 15, the sealing member 16 of the cover body 15 comes into close contact with the peripheral edge of the top surface of the external case 20, and the clamped portion 32d of the port portion 31 is clamped between the cover body 15 and the external case 20, so as to form an air-tightly sealed space between the cover body 15 and the external case 20. This state will be maintained by the engagement between the cover body 15 and the engagement pawl 23 of the external case 20.

Then, the patient-side tube (not shown) is fluidically connected to the port portion 31 of the receptacle 30, and the dial R1 of the regulator R is adjusted to create a negative pressure in the interior spaces of the cover body 15 and the external case 20. In conjunction with the creation of a negative pressure, a negative pressure is also created in the interior space of the receptacle 30 through the air-pervious sheet 38 of the receptacle 30. Thus, the medical suction device 1 can initiate an operation for sucking waste liquid through the patient-side tube.

When the receptacle 30 is discarded after completion of the waste-liquid sucking operation, the creation of a negative pressure is stopped by adjusting the dial R1 of the regulator R. Then, the tongue portion 15e of the cover body 15 is operated to release the engagement between the engagement pawls 15f and 23, and the cover body 15 is rotated in a direction opposite to the arrow Y4 to open the opening 22 of the external case 20.

Then, the receptacle 30 is taken out of the external case 20, and discarded together with the patient-side tube. Based on the function of the check valve of the port portion 31, the receptacle 30 taken out of the external case 20 will be transported without outflow of the sucked waste liquid. Further, the external case 20 is designed to be detached from the holder 10. Thus, after the operation for disposal of the receptacle 30, the external case 20 can be readily cleaned.

As described above, according to the medical suction device 1, the air-pervious sheet 38 surrounded by the cover body 15 and the external case 20 (hereinafter referred to collectively as "rigid case") is designed to discharge an air in the interior space of the receptacle 30 to the interior space of the rigid case. Thus, a negative pressure can be created in the interior space of the receptacle 30 by creating a negative pressure in the interior space of the rigid case. That is, the suction-side tube K2 fluidically connected to the suction source can be fluidically connected to the cover body 15 to create a negative pressure in the respective interior spaces of the rigid case and the receptacle 30. This makes it possible to eliminate the need for attaching the suction-side tube K2 to the receptacle 30 separately or independently.

As above, in the medical suction device 1, the waste-liquid sucking operation can be initiated by attaching only the patient-side tube to the receptacle 30. This makes it possible to reduce a time period required for the preparatory operation and prevent an improper connection of tubes. In addition, the patient-side tube may be attached to the receptacle 30 in advance. This receptacle 30 pre-connected with the patient-side tube can be attached directly to the rigid case to allow a medical staff to perform the setup operation in a more simplified manner.

In an operation for disposal of the collected waste liquid, the receptacle 30 can be detached from the rigid case, without performing an operation for detaching the suction-side tube K2 from the receptacle 30, and discarded together with the patient-side tube connected to the receptacle 30. Thus, a time period required for the disposal operation can be reduced. This also makes it possible to reduce the frequency of contact of a medical staff with a component other than the receptacle 30 and the patient-side tube to be discarded, during the disposal operation, so as to maximally prevent a secondary infection.

In the medical suction device 1, the check valve 34 can prevent the sucked waste liquid from reversely flowing to the patient-side tube to allow the collected waste liquid to be reliably discarded while suppressing infections due to outflow of the collected waste liquid from the receptacle 34.

In the medical suction device 1, the sheet 37 and the air-pervious sheet 38 are surrounded by the rigid case while being air-tightly attached to the rigid case through the outer periphery of the port portion 31 (clamped portion 32d). This makes it possible to suck waste fluid without compression of the receptacle 30 having flexibility, and simplify the structure of the receptacle 30.

In the medical suction device 1, the receptacle 30 has an outer wall formed of the sheet 37 and the air-pervious sheet 38 each having flexibility. Thus, when the receptacle 30 is transported before use, the sheets 37, 38 may be folded or rolled up to take measures to provide a compact transport shape.

In the medical suction device 1, the regulator R is disposed under the bottom portion 21 of the external case 20. That is, the regulator R is disposed at a position where an operation for attaching and detaching the receptacle 30 to/from the external case 20 through the opening 22 is not hindered. This makes it possible to facilitate the operation for attaching and detaching the receptacle 30.

The receptacle body 36 in the above embodiment is formed using the air-pervious sheet 38 having air-perviousness in the entire surface thereof, as shown in FIG. 5A. In place of this structure, the receptacle body 36 may be formed using an air-pervious sheet 138 having an air-pervious portion B1 located below the port portion 31 and at a position corresponding to a target liquid level of sacked waste liquid, as shown in FIG. 5B, or an air-pervious sheet 238 having an air-pervious portion B2 in the entire range below a position corresponding to the target liquid level, as shown in FIG. 5C. For example, means for adjusting the position and/or area of the air-pervious portion B1 or B2 includes partly joining the sheet 37 and the air-pervious sheet 38, and providing the pores of the joining layer 38a of the air-pervious sheet 38 in an area corresponding to the air-pervious portion B1 or B2 while providing no pore in the remaining area. According to the above structure, the air-pervious portion B1 or B2 is formed at a position below the port portion 31 in the state after being held by the rigid case. Thus, the sucked waste liquid can has contact with the entire region of the air-pervious portion B1 or B2 to block off the gas-communication between the receptacle 30 and the rigid case, while opening the interior space of the receptacle 30 to atmospheric pressure through the patient-side tube, so as to automatically stop the suction of waste liquid. This makes it possible to stop the suction of waste liquid before waste liquid is sucked up to a liquid level corresponding to the port section 31 so as to prevent the sucked waste liquid from reversely flowing to the patient-side tube. In particular, when the air-pervious portion is formed at a position corresponding to the target liquid level, as in the air-pervious portion B1, the suction of waste liquid can be automatically stopped at a time when waste liquid is sucked up to the target level. Further, when the air-pervious portion is formed in the entire range located below the target liquid level, as in the air-pervious portion B2, a negative pressure can be effectively created in the interior space of the receptacle 30 by utilizing the entire region of the air-pervious portion B2, just after initiation of the sucking operation.

Figure 6A:
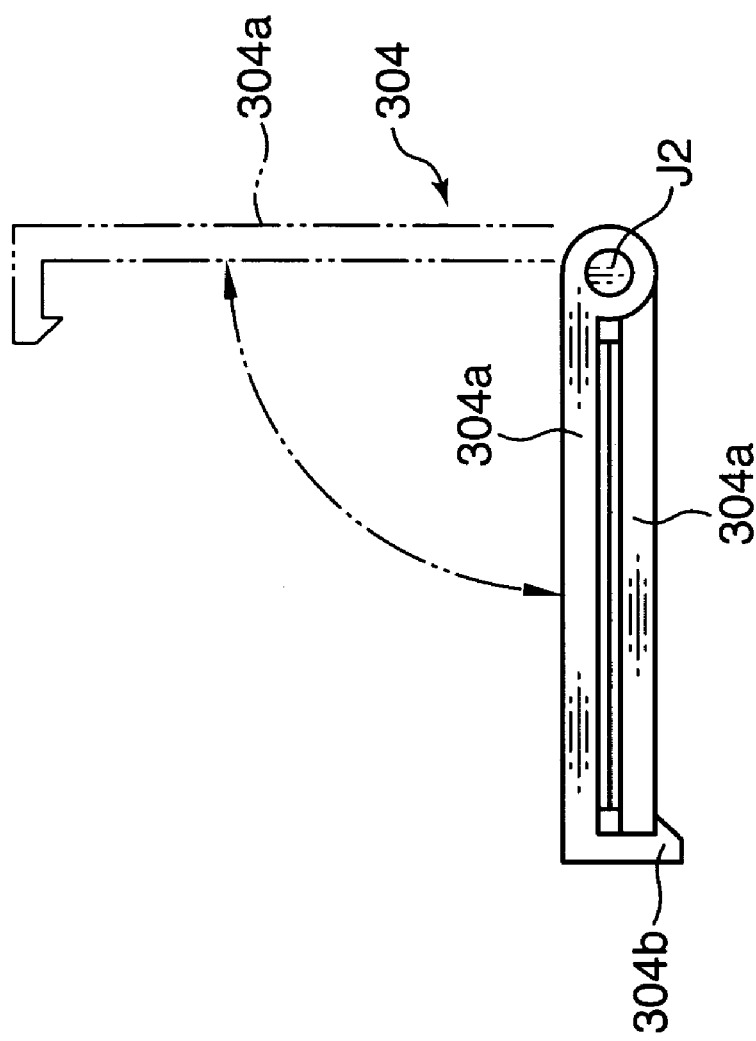
Figure 6B:
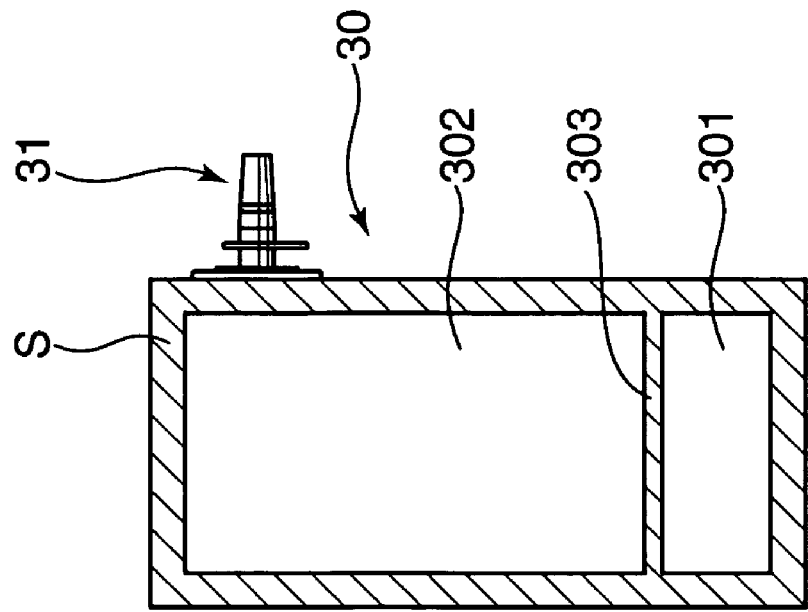

Further, as shown in FIG. 6A, a partition portion 303 may be formed in the receptacle 30 to partition the interior space of the receptacle 303 into a coagulating-agent storage chamber 301 for storing a coagulating agent for coagulating the sacked waste liquid, and a waste-liquid receiving chamber 302 for receiving waste liquid therein. For example, this partition portion 303 may be a weakly sealed portion formed by joining the sheet 37 and the air-pervious sheet 38 with a bonding strength less than that in the peripheral edge S. In a receptacle employing this weakly sealed portion, a medical staff can manually press the waste-liquid receiving chamber 302 during disposal of the receptacle 30, to increase an internal pressure of the waste-liquid receiving chamber 302, and release the weakly sealed portion based on the increased pressure, so as to provide fluid communication between the coagulating-agent storage chamber 301 and the waste-liquid receiving chamber 302. Alternatively, the partition portion 303 may be formed by a clamp member 304 as shown in FIG. 6B. This clamp member 304 comprises a pair of clamp segments 304a swingable about a swing axis J2 located at a base end of each of the clamp segments 304a, and an engagement piece 304 adapted to allow respective distal ends of the clamp segments to be detachably engaged with one another. The clamp segments 304a are designed to pressingly clamp the sheet 37 and the air-pervious sheet 38 therebetween. The clamp member 304 is used in such a manner as to, during suction of waste-liquid, pressingly clamp the sheet 37 and the air-pervious sheet 38 to form the partition portion 303, and, during disposal of the receptacle 30, release the engagement based on the engagement piece 304b to provide fluid communication between the coagulating-agent storage chamber 301 and the waste-liquid receiving chamber 302.

According to the above medical suction device, the collected waste liquid can be coagulated. This makes it possible to prevent leakage of the waste liquid during transportation of the receptacle 30 after completion of the waste-liquid collecting operation, and subject the coagulated waste liquid to a treatment, such as incineration.

Further, according to the above medical suction device, the coagulating agent can be fed in waste liquid according to need. Thus, it can be appropriately determined whether sucked waste liquid should be coagulated, depending on a volume of the waste liquid.

A receptacle according to another embodiment of the present invention will be described below.

Figure 7:
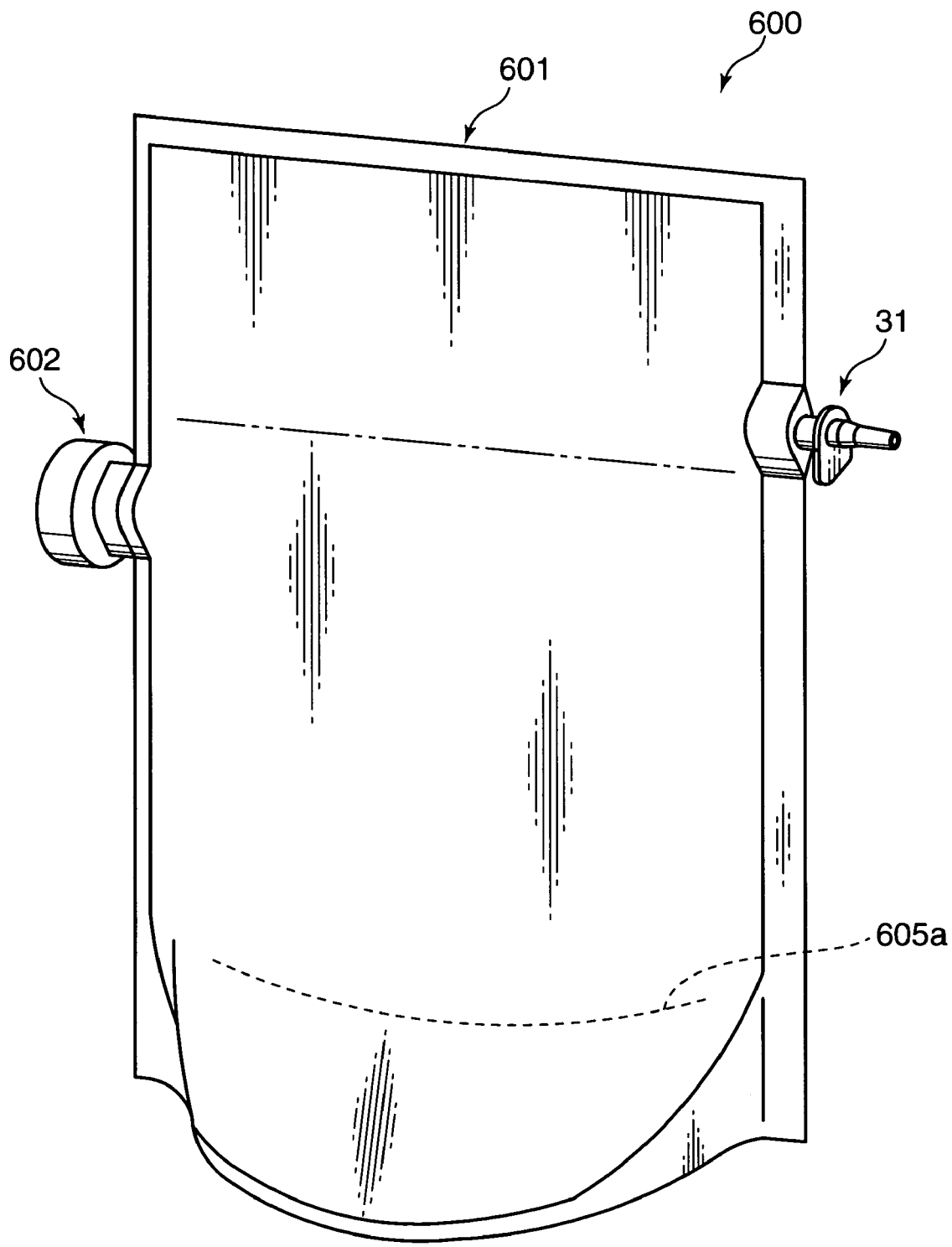
FIG. 7 is a perspective view showing the entire structure of a receptacle according to yet anther embodiment of the present invention.
Figure 8:
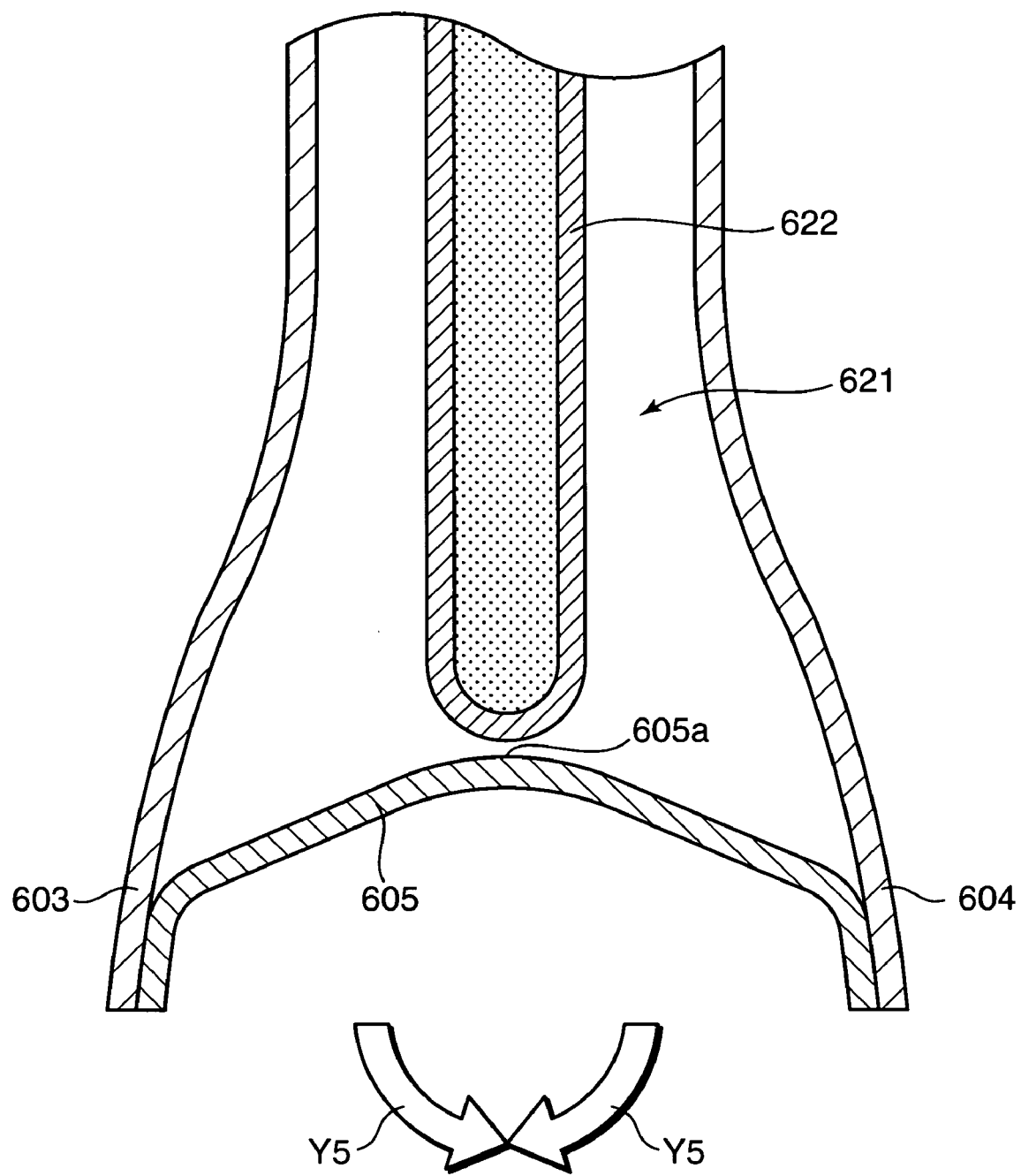
FIG. 8 is a fragmentary sectional side view showing the receptacle in FIG. 7.
Figure 9:
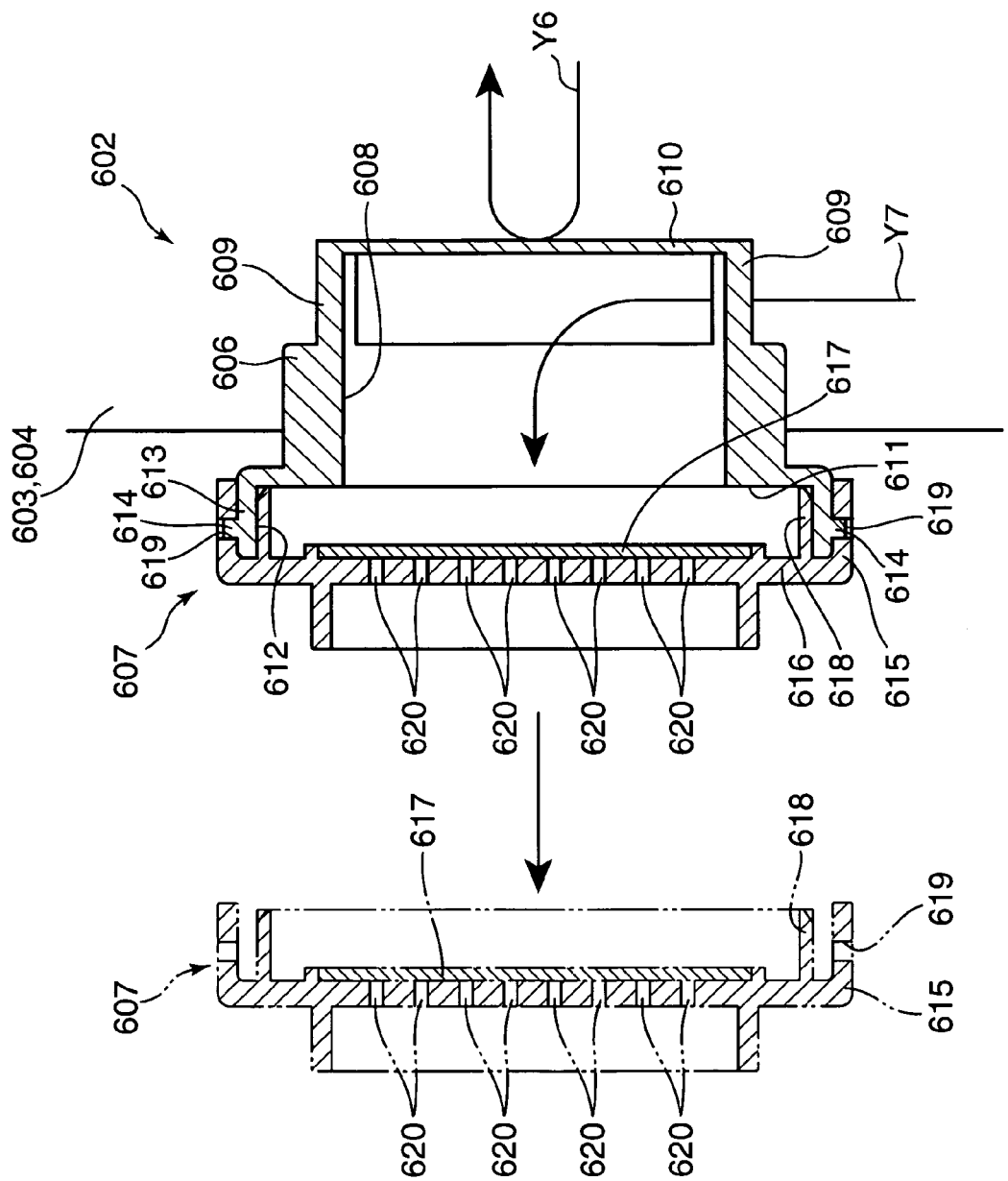
FIG. 9 is a sectional front view showing an air-pervious unit of the receptacle in FIG. 7.

FIG. 7 is a perspective view showing the entire structure of a receptacle 600 according to anther embodiment of the present invention. FIG. 8 is a fragmentary sectional side view showing the receptacle 600 in FIG. 7, and FIG. 9 is a sectional front view showing an air-pervious unit 602 of the receptacle 600 in FIG. 7.

Referring to these figures, the receptacle 600 comprises the port portion 31, a receptacle body 601 for receiving therein waste liquid sucked through the port portion 31, an air-pervious unit 602 in fluid communication with an interior space of the receptacle body 601, and a coagulating-agent packed module 621 housed in the receptacle body 601. The port portion 31 has the same structure as that described above, and its description will be omitted herein.

The receptacle body 601 comprises a pair of opposed rectangular-shaped sheets 603, 604 joined together along three edges thereof, and a bottom sheet 605 joined to the sheets 603, 604 along remaining one edge thereof to close an opening between the sheets 603, 604. The receptacle body 601 is generally formed to have a bag shape.

The bottom sheet 605 can be folded in a direction indicated by the arrow Y5 along a ridge line 605a formed by a configuration protruding toward the inward side of the receptacle 601 at an intermediate position between and in an opposed direction of the rectangular sheets 603, 604. That is, this ridge line 605a allows the receptacle body 601 to be changed in shape between a developed shape where the receptacle body 601 is self-standing, as shown in FIG. 7, and a planar shape where the rectangular sheets 603, 604 is in close contact with one another.

Each of the sheets 603 to 605 has a 3-layer structure formed by laminating a polyethylene layer, a polyamide (nylon) layer and a PET (polyethylene terephthalate) layer in this order from the inward side of the receptacle body 601, and the sheets 603 to 605 are joined to each other through their polyethylene layers.

The port portion 31 and the air-pervious unit 602 are disposed, respectively, on opposed lateral edges of the receptacle body 601, and joined between the rectangular sheets 603, 604. In this arrangement, the air-pervious unit 602 is located below a position of the port portion 31 (indicated by the two-dot chain line in FIG. 7).

The air-pervious unit 602 comprises a communication pipe (communication member) 606 joined between the rectangular sheets 603, 604, and a closing member 607 detachably attached to one end of the communication pipe 606.

The communication pipe 606 includes: an inner cavity 608 serving as a passage providing fluid communication between interior and exterior spaces of the receptacle body 601; a baffle plate 610 connected to the communication pipe 606 through a plurality of ribs protruding toward the interior space of the receptacle body 601; and a connection tube 613 having a large-diameter cavity 612 which is fluidically connected concentrically to the inner cavity 601 through a shoulder 611.

The ribs 609 are formed intermittently in a circumferential direction of the communication pipe 606, and the baffle plate 610 is disposed to extend in a direction orthogonal to an axis of the inner cavity 608. This structure prevents waste liquid sucked into the interior space of the receptacle body 601 from being introduced directly from the port portion 31 to the inner cavity 608, as indicated by the arrow Y6, and allows the sucked waste liquid to be introduced in the inner cavity 608 through a gap between the adjacent ribs 609, as indicated by the arrow Y7.

The connection tube 613 is disposed outside or in the exterior space of the receptacle body 601, and formed to have a cylindrical shape with the large-diameter cavity 612. The connection tube 613 has an outer peripheral surface formed with a plurality of engagement protrusions 614 protruding outward and intermittently in a circumferential direction thereof.

The closing member 607 includes an external tube 615 fitted onto the connection tube 613, and an air-pervious sheet (air-pervious/liquid-impervious element) 617 joined to a bottom 616 of the external tube 615.

The external tube 615 includes a guide tube 618 protruding from the bottom 616 thereof in such a manner as to be fitted into the large-diameter cavity 612, and designed to clamp the connection tube 613 between an outer peripheral surface of the guide tube 618 and an inner peripheral surface of the external tube 615, while providing airtightness based on these outer and inner peripheral surfaces.

Further, the external tube 615 is formed with a plurality of engagement holes 619 engageable with the corresponding engagement protrusions 614, and a plurality of expanded portions (not shown) each having an inner diameter greater than each outer diameter of the engagement protrusions 614. The engagement holes 619 and the expanded portions are alternately formed in the circumferential direction of the external tube 615. Thus, a medical staff can rotate the external tube 615 engaged with the communication pipe 606, to detach the closing member 607 from the communication pipe 606, as indicated by the two-dot chain line in FIG. 9.

If the closing member 607 is detached in the above manner, the collected waste liquid in the receptacle body 601 can be discharged outside through the communication pipe 606.

The air-pervious sheet 617 is made of a material having air-perviousness and liquid-imperviousness (e.g. lamination of polysulfone and polyurethane), and joined to the bottom 616 to allow gas in the interior space of the receptacle body 601 to be discharged through a plurality of through-holes 620 formed in the bottom 616. Thus, in response to the creation of a negative pressure in the interior space of the external case, gas in the interior space of the receptacle body 601 will be discharged outside through the inner cavity 608, the air-pervious sheet 617 and the through-holes 620 in this order.

The coagulating-agent encased module 621 comprises the aforementioned coagulating agent for coagulating waste liquid, and an encasing member 622 for encasing the coagulating agent.

The encasing member 622 is made of a water-soluble or water-decomposable material which is optionally subjected to a given treatment, such as coating, according to need. When the encasing member 622 comes in contact with waste liquid, it can be solved (decomposed) to release the coagulating agent therefrom.

The receptacle 600 constructed as above can be folded as shown in FIG. 10 to obtain a compact shape suitable for wrapping or packaging.

FIGS. 10A to 10D are top plan view showing a process of folding the receptacle 600 illustrated in FIG. 7.

Firstly, the bottom sheet 605 is folded along the ridge line 605a (see FIG. 8) to form the receptacle 600 in a planer shape.

Then, as shown in FIG. 10A, a portion of the receptacle 600 above the port portion 31 is folded along a folding line O1 parallel to a width direction of the receptacle 600. Then, as shown in FIG. 10B, the folded portion is further folded inward along a folding line O2 parallel to the folding line O1 at an intermediate position between the folding line O1 and the port portion 31.

Referring to FIG. 10C, the receptacle 600 is subjected to mountain fold and valley fold along each of folding lines O3, O4 (linger edges of the housed coagulating-agent encasing module 621) parallel to a longitudinal direction of the receptacle 600 (i.e., the receptacle body 601 is folded in a zig-zag manner). Then, a pair of upper and lower tapes (fastening element) TP are attached to maintain the folded shape, as shown in FIG. 10D.

These tapes TP are attached to allow triply superimposed portions of the receptacle 601 around the folding lines O3, O4 to come into close contact with each other so as to prevent the receptacle 601 from being unfolded. Further, each of the tapes TP has an adhesive force adjusted to cause peeling in response to an after-mentioned expansion of the receptacle 600.

Figure 11:
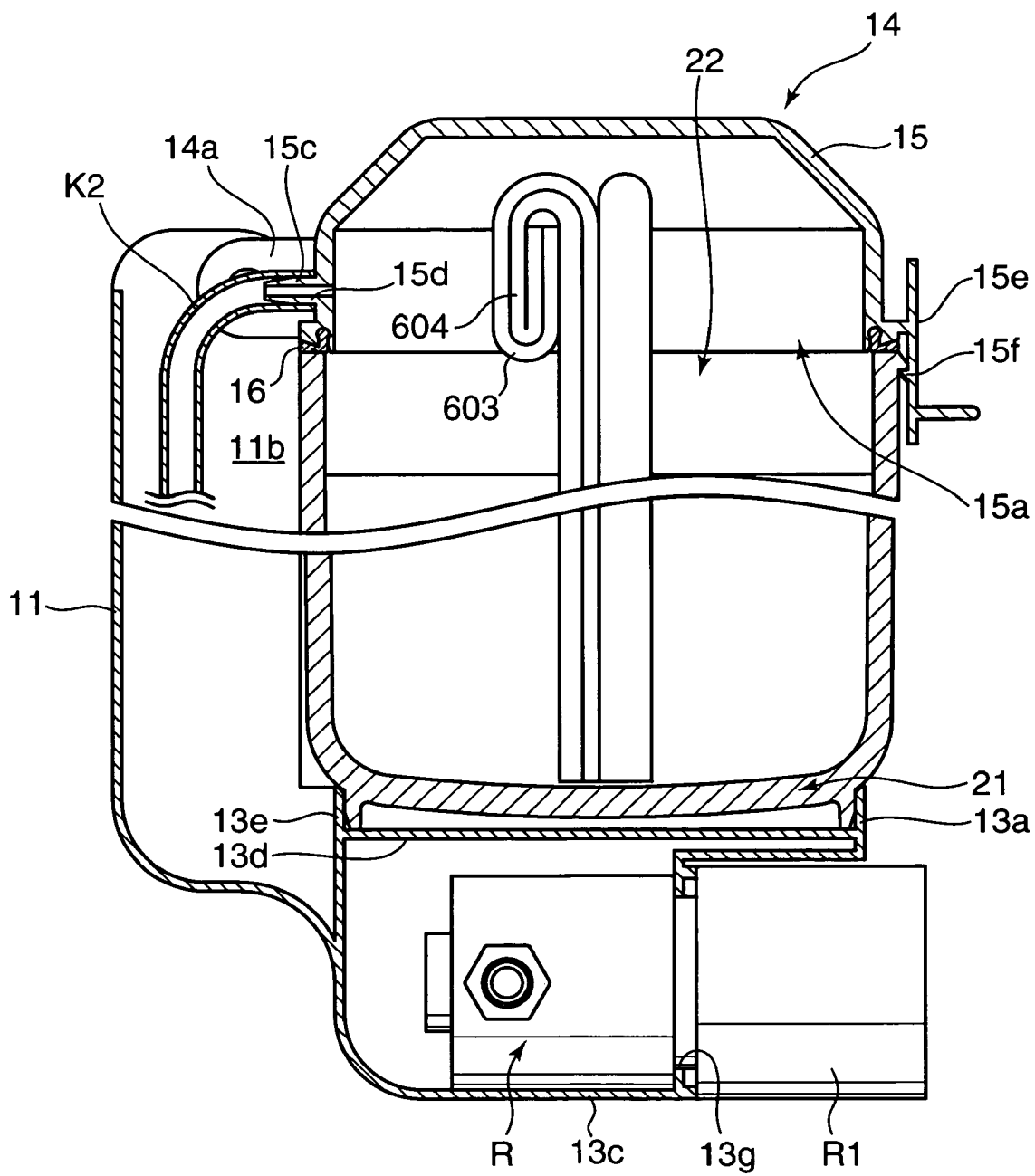
FIG. 11 is a sectional side view showing the state before suction of waste liquid in a process of sucking waste fluid using the receptacle in FIG. 7.
Figure 12:
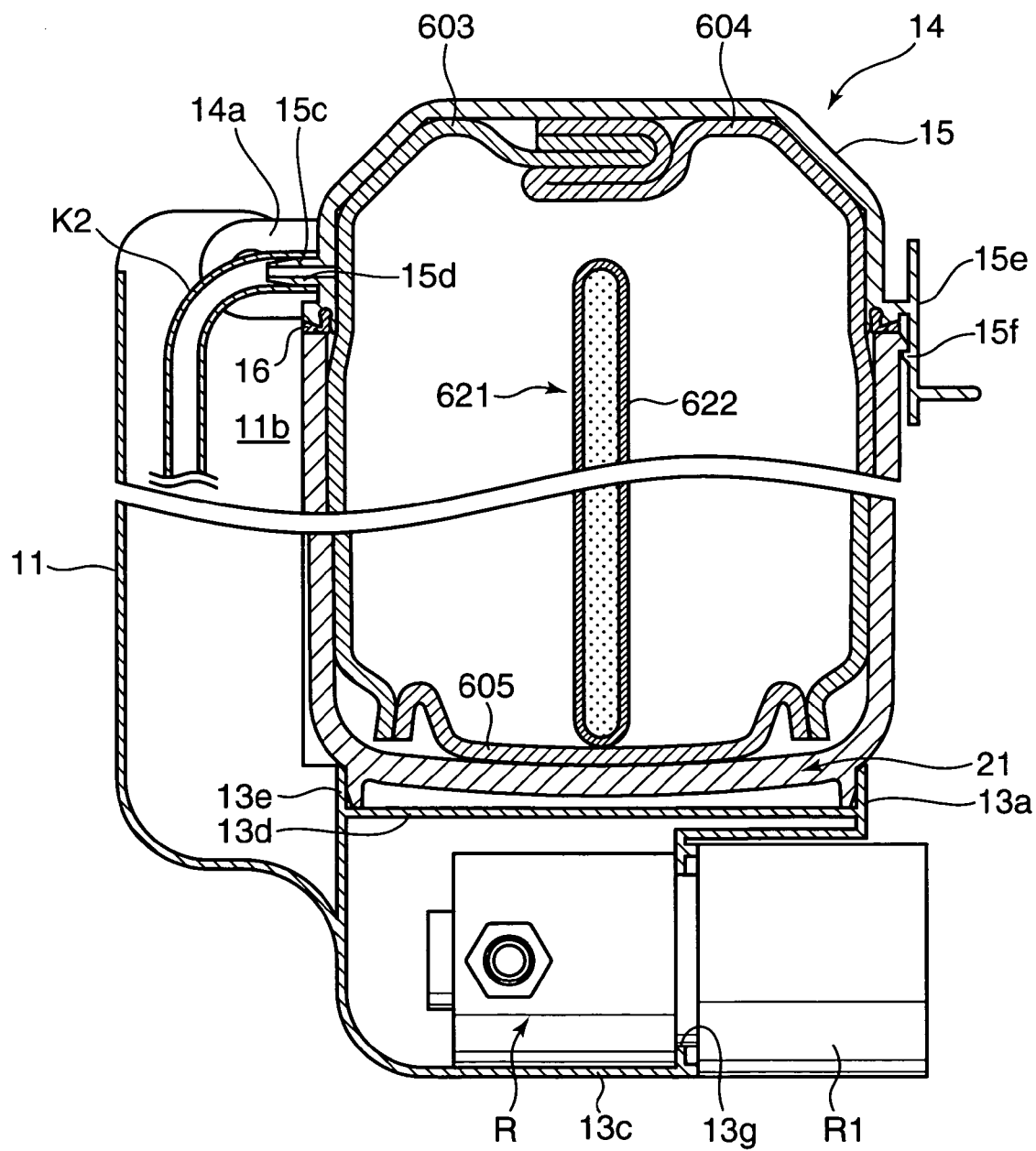
FIG. 12 is a sectional side view showing the state after a negative pressure is created in an interior space of an external case in the process of sucking waste fluid using the receptacle in FIG. 7.
Figure 13:
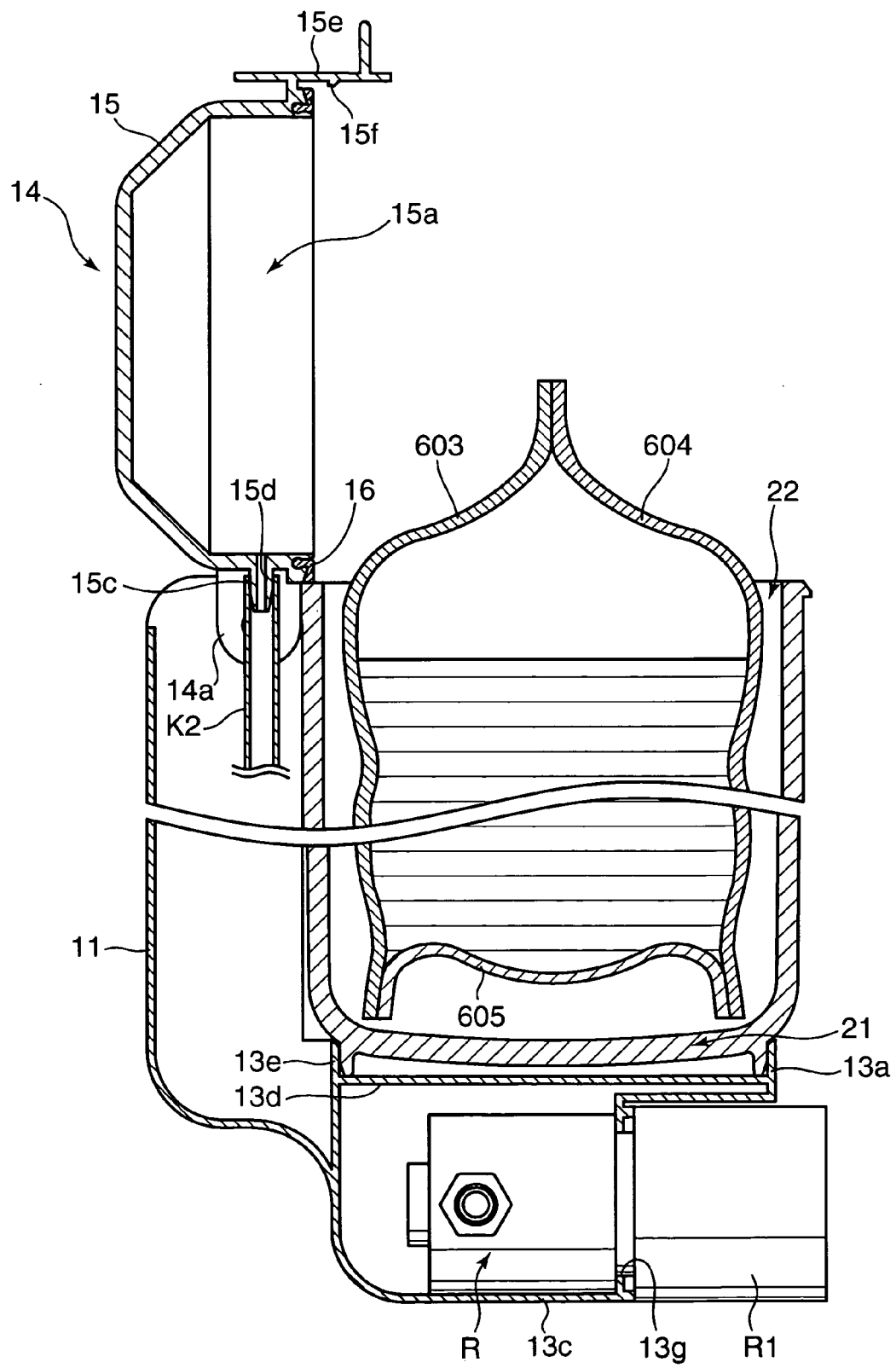
FIG. 13 is a sectional side view showing the state after suction of waste liquid in the process of sucking waste fluid using the receptacle in FIG. 7.

With reference to FIGS. 11 to 13, a method of use of the above receptacle 600 will be described below. As to a part of the method overlapping with that of the receptacle 30, its description will be omitted.

As shown in FIG. 11, the receptacle 600 folded in the above manner is set up in the external case 20 attached to the medical suction device 1, while maintaining the folded shape, and the opening 22 of the external case 20 is closed by the cover body 15. In this process, the air-pervious unit 602 of the receptacle 600 is disposed within the external case 20.

Then, when a negative pressure is created in the interior space of the cover body 15 and the external case 20, the receptacle 600 expands in such a manner as to come into close contact with an inner surface of the external case 20, as shown in FIG. 12.

Specifically, in an initial stage of creating a negative pressure, a pressure in a space between the cover body 15/the external case 20 and the receptacle 600 is sharply reduced, and gas in the interior space of the receptacle 600 is gradually discharged through the air-pervious sheet 617 due to a resistance of the air-pervious sheet 617 to gas flow. Thus, an internal pressure of the receptacle 600 becomes relatively greater than the external pressure, and the tapes TP will be peeled in response to expansion of the receptacle 600 caused by the resulting pressure difference.

Further, as shown in FIG. 12, a portion of the receptacle 600 folded along the folding lines O1, O2 is brought into contact with the cover body 15, and pressed onto the cover body 15 while maintaining its folded state. Thus, a space corresponding to this folded portion is maintained as an unexpanded portion (dead space: one example of pressure reduction means).

In other words, a longitudinal dimension of the rectangular sheets 603, 604 are arranged at a large value sufficient to allow the receptacle 600 to be brought into contact with the cover body 15 so as to prevent the receptacle 600 from being fully unfolded.

Then, after completion of the waste-liquid sucking operation, the cover body 15 is opened to allow the folded portion of the receptacle 600 in contact with the cover body 15 to be unfolded, as shown in FIG. 13. Thus, a volume of the interior space of the receptacle 600 is increased. This allows a residual pressure of the receptacle 600 to escape into a space having the increased volume so as to provide a reduced residual pressure.

As above, according to the receptacle 600, an unexpanded portion can be maintained during the waste-liquid sucking operation. This makes it possible to reduced an internal pressure of the receptacle 600 which is otherwise increased due to fluid (air or waste liquid) to be trapped in the receptacle 600 by the check valve 34 after completion of the waste-liquid collecting operation, so as to prevent close contact between the receptacle 600 and the external case 20 to allow the receptacle 600 to be readily taken out of the external case 20.

While the receptacle 600 are designed to be brought into contact with the cover body 15 based on an increased longitudinal dimension of the rectangular sheets 603, 604, so as to form the dead space, the present invention is not limited to this manner. For example, during the waste-liquid sucking operation, the dead space may be maintained in the receptacle body 601 by temporarily fusion-bonding the rectangular sheets 603, 604 in a peelable manner to prevent a folded portion from being unfolded, or by partitioning the interior space of the receptacle body 601 into two receiving chambers using the aforementioned clamp member 340 or weakly sealed portion (see FIG. 6).

When the receptacle is constructed in this way, a medical staff will manually perform an operation for releasing or opening the temporarily-fusion-bonded potion or the clamp member or the weakly-sealed portion, after the waste-liquid collecting operation, to increase an internal volume of the receptacle body 601.

While the receptacle 600 is designed to increase an internal volume of the receptacle body 601 so as to release a residual pressure of the receptacle body 601, the present invention is not limited to this manner. For example, the receptacle 600 may be provided with a valve adapted to selectively open the interior space of the receptacle body 601 to the outside air.

According to the receptacle including the air-pervious unit attached to the receptacle body 601, comparing with the receptacle body composed of the sheets 603 to 605 integrally formed with the air-pervious/liquid-impervious element, the sheets 603 to 605 may be formed at a lower cost.

In addition, this receptacle has no need for integrally forming the air-pervious sheet 617 in one or more of the sheets 603 to 605. This makes it possible to form the sheets 603 to 605 using one appropriately selected from a plurality of materials suitable for being formed into a bag shape, so as to avoid restrictions on sheet production processes which would otherwise occur when the air-pervious sheet 617 is integrally formed with one or more of the sheets 603 to 605.

According to the receptacle using the tapes TP, a folded portion of the receptacle 600 can be maintained or prevented from being unfolded, to provide a compact shape during packaging or the like. In addition, the tapes TP are peeled (the fastened state of the folded portion is released) in response to expansion of the receptacle 600. Thus, even if the receptacle 600 is inserted into the interior space of the external case 20 while maintaining the packaged shape, the receptacle 600 can be returned to its original unfolded state in response to a negative pressure in the interior space of the external case 20.

While the receptacle 600 employs the tapes TP for fastening the folded portion of the receptacle body 601 to prevent the folded portion from being unfolded, the present invention is not limited to this manner, but the rectangular sheets 603, 604 may be temporarily fusion-bonded together in a peelable manner to prevent a folded portion of the receptacle body 601 from being unfolded.

Figure 14:
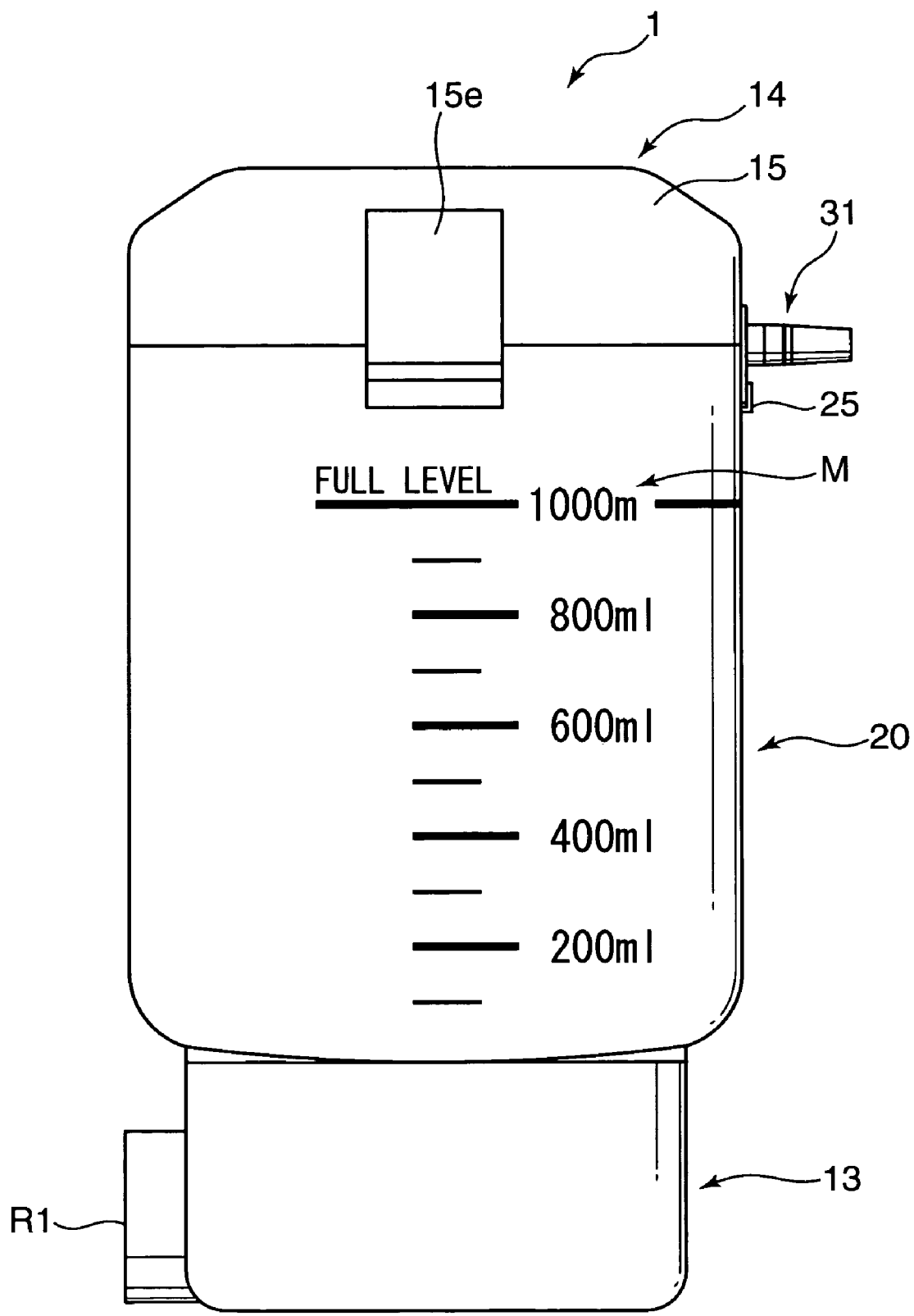
FIG. 14 is a front view showing a medical suction device according to another embodiment of the present invention.

Further, as shown in FIG. 14, the medical suction device 1 may be appropriately modified such that the external case 20 is made of a light-transmittable material and formed with a scale portion M for indicating a suction volume corresponding a liquid level of a waste liquid collected in the internal space of the receptacle 30, so as to allow a user to visually check the receptacle 30 from outside, or the dial R1 of the regulator R is disposed to protrude from a lateral surface of the mounting/storage portion 13.

Figure 15:
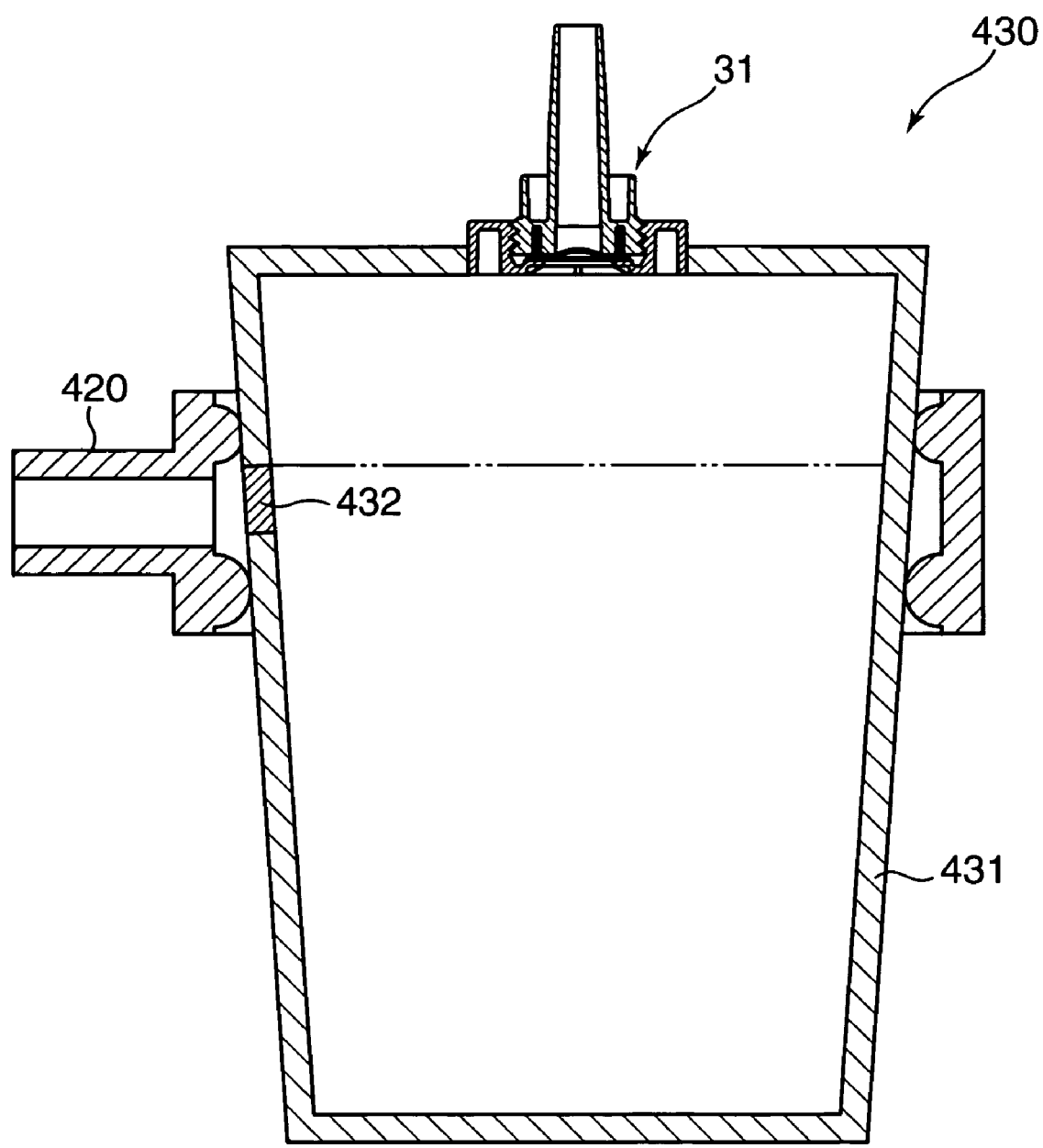
FIG. 15 is a sectional view showing a receptacle according to still anther embodiment of the present invention.

While each of the receptacle bodies 31, 601 in the above embodiments comprises a sheet-shaped component, the receptacle body may be made of a material having rigidity, as shown in FIG. 15. In this case, a receptacle 430 comprises an approximately circular truncated cone-shaped receptacle body 431 having rigidity, a port portion 31 fluidically connected to the receptacle body 431, and an air-pervious portion 432 incorporated in a lateral wall of the receptacle body 431 at a position corresponding to a target liquid level of waste liquid. The air-pervious portion 432 may have the same structure as that of the air-pervious sheet 38. In the use of this receptacle 430, a negative pressure is created in at least a region formed of the air-pervious portion 432 (a region surrounding a portion of the air-pervious portion 432 formed of the receptacle body 431). Then, in response to this created negative pressure, a negative pressure is also created in an interior space of the receptacle body 431. Thus, a medical staff can suck waste liquid using a patient-side tube (not shown) fluidically connected to the port portion 31. That is, when the receptacle body 431 is formed to have a certain level of rigidity capable of preventing deformation thereof due to the negative pressure of the external case 420, the waste-liquid sucking operation can be performed by creating a negative pressure in at least the region formed of the air-pervious portion 432.

Figure 16:
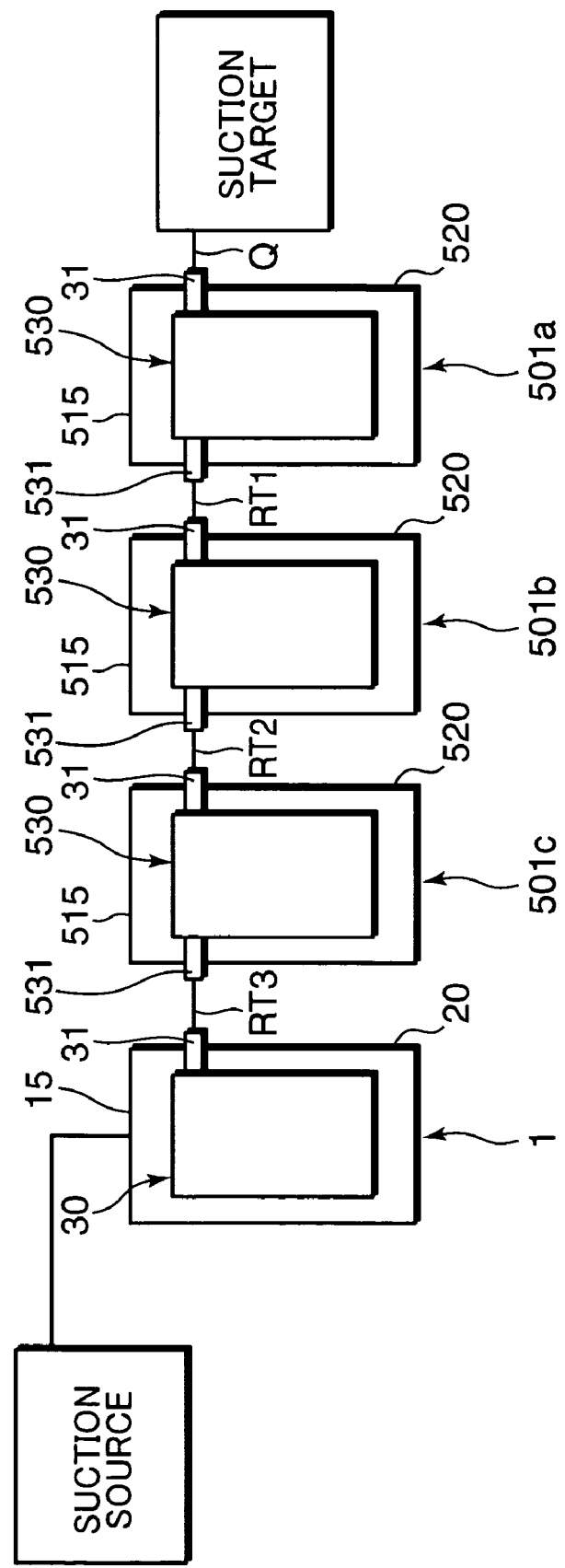
FIG. 16 is a schematic diagram showing a medical suction device and a plurality of connectable suction devices, which are fluidically connected together to suck a large volume of waste liquid.

Furthermore, as shown in FIG. 16, when it is supposed that a large amount of waste liquid has to be sucked, the aforementioned medical suction device 1 may be coupled to one or more connectable suction devices 501 to perform a waste-liquid sucking operation. Specifically, each of the connectable suction devices 501 comprises a receptacle 530 having the aforementioned sheet 37 and the aforementioned air-pervious sheet 38. The receptacle 530 includes the port portion 31, and a discharge port 531 adapted to discharge waste liquid collected in an interior space between the sheets 37, 38. Further, the connectable suction device 501 includes a cover body 515 and an external case 520, which have a mechanism (equivalent to the aforementioned cutout portions 15b, 24) for air-tightly clamping and holding the discharge port 531 therebetween, in addition to the aforementioned structures of the cover body 15 and the external case 20. In FIG. 16, the connectable suction devices are defined by reference numerals 501a, 501b, 501c in order from an upstream side of a flow of sucked waste liquid (or from the side of a suction target).

For example, when the medical suction device 1 is used in combination with three of the connectable suction devices 501, the medical suction device 1 is disposed on the downmost stream of a sucked waste liquid flow, the port portion 31 of the medical suction device 1 is fluidically connected to the discharge port 531 of the connectable suction device 501c through a connection tube RT3. Further, a port portion 31 of the connectable suction device 501c is fluidically connected to the discharge port 531 of the connectable suction device 501b through a connection tube RT2, and a port portion 31 of the connectable suction device 501b is fluidically connected to the discharge port 531 of the connectable suction device 501a through a connection tube RT1. Then, a patient-side tube Q is fluidically connected to a port portion 31 of the connectable suction device 501a, and the interior space of the rigid case (or the interior space of the cover body 15 and the external case 20) is fluidically connected to a suction source).

When a negative pressure is created in the interior space of the rigid case of the medical suction device 1 by the suction source, a negative pressure is created in the interior space of the receptacle 30 through the air-pervious sheet 38, and then a negative pressure is sequentially created in respective interior spaces of the receptors 530 fluidically connected to the receptacle 30 through the connection tubes RT1 to RT3. Thus, a negative pressure is also sequentially created in respective interior spaces of the rigid case (or respective interior spaces of the cover bodies 515 and the external cases 520) of the connectable suction devices 501a to 501c to allow waste liquid to be sucked from the patient-side tube Q. In this arrangement, when waste liquid is sucked using the patient-side tube Q, the waste liquid flows into the interior space of the receptacle 530 of the connectable suction device 501a. Then, when the waste liquid is sucked up to an allowable volume of this receptacle 530, a subsequently sucked waste liquid flows into the interior space of the receptacle 530 of the connectable suction device 501b through the discharge port 531 and connection tube RT1. Then, the waste liquid flows into the interior space of the receptacle 530 of the connectable suction device 501c through the discharge port 531 and connection tube RT2, and then flows into the interior space of the receptacle 30 of the medical suction device 1 through the connection tube RT3.

As above, the medical suction device 1 is used in combination with three of the connectable suction devices 501, a large volume of waste liquid can be sucked without the need for providing means for creating a negative pressure in respective interior spaces of the rigid cases of the connectable suction devices 501a to 50c independently. Further, in an operation for disposal of the collected waste liquid, each of the receptacle 30 and receptacles 530 is detached from a corresponding one of the external cases 20, 520, and all of the receptacle 30, the receptacles 530, the connection tubes RT1 to RT3 and the patient-side tube Q can be collectively discarded. That is, comparing with a case where means for creating a negative pressure in respective interior spaces of the rigid cases and the receptacles is attached to the connectable suction devices independently or separately, the receptacles 530 each employing the air-pervious sheets 38 make it possible to provide enhanced efficiency of a preparatory operations for the connectable suction devices 501.

As mentioned above, a region of the receptacle to be surrounded by the rigid case has the air-pervious/liquid-impervious element adapted to discharge an air in the interior space of the receptacle to the interior space of the rigid case in response to a negative pressure created in the interior space of the rigid case. Thus, through the creation of a negative pressure in the interior space of the rigid case, a negative pressure can also be created in the interior space of the receptacle. That is, in order to create a negative pressure in both the interior spaces of the rigid case and the receptacle, means for creating a negative pressure can be attached to only the rigid case. This makes it possible to eliminate the need for attaching the negative-pressure creating means to the receptacle independently or separately.

Thus, the operation for sucking waste liquid can be initiated by attaching only the patient-side tube to the receptacle. This makes it possible to reduce a time period required for the preparatory operation and prevent an improper connection of tubes. In addition, the patient-side tube may be attached to the receptacle in advance. This receptacle pre-connected with the patient-side tube can be attached directly to the rigid case to allow a medical staff to perform the setup operation in a more simplified manner.

In an operation for disposal of the collected waste liquid, the receptacle can be discarded simply after being detached from the rigid case, without performing an operation for detaching from the rigid case means for creating a negative-pressure in the interior space of the receptacle as in the conventional manner. Thus, a time period required for the disposal operation can be reduced. This also makes it possible to reduce the frequency of contact of a medical staff with a component other than the receptacle and the patient-side tube to be discarded, during the disposal operation, so as to maximally prevent a secondary infection.

Specifically, a receptacle for use with a medical suction device which is equipped with a rigid case for detachably holding and air-tightly surrounding at least a portion of the receptacle, and a patient-side tube for introducing waste liquid into the receptacle, and designed to create a negative pressure in both an interior space of the rigid case and an interior space of the receptacle so as to allow waste liquid to be sucked into the receptacle through the patient-side tube. The receptacle comprises an air-pervious/liquid-impervious element having air perviousness and liquid imperviousness. The air-pervious/liquid-impervious element at least partly constitutes at least the portion of the receptacle to be surrounded by the rigid case. Further, the air-pervious/liquid-impervious element is adapted to discharge an air in the interior space of the receptacle to the interior space of the rigid case in response to the negative pressure created in the interior space of the rigid case.

With this construction, a region of the receptacle to be surrounded by the rigid case has the air-pervious/liquid-impervious element adapted to discharge an air in the interior space of the receptacle to the interior space of the rigid case in response to the negative pressure created in the interior space of the rigid case. Thus, through the creation of a negative pressure in the interior space of the rigid case, a negative pressure can also be created in the interior space of the receptacle. That is, in order to create a negative pressure in both the interior spaces of the rigid case and the receptacle, means for creating a negative pressure can be attached to only the rigid case. This makes it possible to eliminate the need for attaching the negative-pressure creating means to the receptacle independently or separately.

As above, in the receptacle, the operation for sucking waste liquid can be initiated by attaching only the patient-side tube to the receptacle. This makes it possible to reduce a time period required for the preparatory operation and prevent an improper connection of tubes. In addition, the patient-side tube may be attached to the receptacle in advance. This receptacle pre-connected with the patient-side tube can be attached directly to the rigid case to allow a medical staff to perform the setup operation in a more simplified manner.

In an operation for disposal of the collected waste liquid, the receptacle can be discarded simply after being detached from the rigid case, without performing an operation for detaching from the rigid case means for creating a negative-pressure in the interior space of the receptacle as in the conventional manner. Thus, a time period required for the disposal operation can be reduced. This also makes it possible to reduce the frequency of contact of a medical staff with a component other than the receptacle and the patient-side tube to be discarded, during the disposal operation, so as to maximally prevent a secondary infection.

In the receptacle, a gas-communication path between the receptacle and the rigid case is blocked off at a time when waste liquid is sucked and the sucked waste liquid has contact with the entire region of the air-pervious/liquid-impervious element. This means that the interior space of the receptacle is opened to atmospheric pressure at that time. That is, the suction of waste liquid can be stopped at the time when the sucked waste liquid has contact with the entire region of the air-pervious/liquid-impervious element. Differently from the conventional receptacle, this makes it possible to eliminate the need for additionally providing a member for stopping the creation of a negative pressure, so as to achieve reductions in the number of components and in cost.

Preferably, the receptacle further includes a check valve adapted to allow waste liquid sucked from the patient-side tube to flow into the interior space thereof, and prevent the sucked waste liquid from flowing out to the patient-side tube.

According to this feature, the check valve can prevent the sucked waste liquid from reversely flowing to the patient-side tube to allow the collected waste liquid to be reliably discarded while suppressing infections due to outflow of the collected waste liquid from the receptacle.

In the receptacle, it is preferable that the air-pervious/liquid-impervious element is located below a connection position with the patient-side tube in the state after being held by the rigid case.

According to this feature, the air-pervious/liquid-impervious element is located below a connection position with the patient-side tube in the state after being held by the rigid case or in the state after being set up in a usable position. Thus, the sucked waste liquid can has contact with the entire region of the air-pervious/liquid-impervious element to block off the gas-communication between the receptacle and the rigid case so as to automatically stop the suction of waste liquid. This makes it possible to stop the suction of waste liquid before waste liquid is sucked up to a liquid level corresponding to the above connection position so as to prevent the sucked waste liquid from reversely flowing to the patient-side tube.

In the above receptacle, it is preferable that the air-pervious/liquid-impervious element is located at a position corresponding to a liquid level for a target suction volume of waste liquid, in the state after being held by the rigid case.

According to this feature, the suction of waste liquid can be automatically stopped at a time when the target suction volume of waste liquid is sucked, for example, at a time when waste liquid is sucked up to a liquid level corresponding to a maximum volume of waste liquid capable of being collected in the receptacle.

In the above receptacle, it is preferable that the air-pervious/liquid-impervious element is located over a given range below the liquid level for the target suction volume of waste liquid, in the state after being held by the rigid case.

According to this feature, just after initiation of the suction, a negative pressure can be effectively created in the interior space of the receptacle by utilizing the entire region of the air-pervious/liquid-impervious element. Further, the suction of waste fluid can be automatically stopped at a time when waste liquid is sucked up to the liquid level for the target suction volume.

Preferably, the above receptacle further includes pressure reduction means for reducing a residual pressure in the interior space thereof after completion of the waste-liquid collecting operation.

After completion of the waste-liquid collecting operation or after the sucked waste liquid has contact with the entire region of the air-pervious/liquid-impervious element, the fluid (gas or waste liquid) is trapped in the interior space of the receptacle by the action of the check valve, and the receptacle is likely to expand due to increase in the internal pressure thereof and come into close contact with an inner surface of the rigid case. However, according to the above feature, the internal pressure can be reduced by the pressure reduction means to prevent the close contact with the rigid case.

Thus, this receptacle can be readily taken out of the rigid case after completion of the waste-liquid collecting operation.

In the above receptacle, it is preferable that the pressure reduction means is adapted to increase a volume of the interior space of the receptacle so as to reduce the residual pressure.

According to this feature, the internal pressure of the receptacle can be reduced by a relatively simple structure, for example, where a portion of the receptacle is formed as a dead space having no expansion during the waste-liquid sucking operation, and the dead space is opened after completion of the waste-liquid collecting operation.

Preferably, the above receptacle comprises a first sheet having air-imperviousness and liquid-imperviousness, a second sheet including the air-pervious/liquid-impervious element and having a peripheral edge joined to a peripheral edge of the first sheet, and a rigid port portion joined between the first and second sheets and adapted to form a part of a passage for introducing waste liquid between the first and second sheets, wherein the receptacle is designed to allow the first and second sheets to be entirely surrounded by the rigid case while air-tightly attaching an outer peripheral surface of the port portion to the rigid case.

According to this feature, the receptacle comprising the first and second sheets or having flexibility is designed to allow the first and second sheets to be entirely surrounded by the rigid case while being air-tightly attached to the rigid case through the rigid port portion. This makes it possible to suck waste fluid without compression of the receptacle, and simplify the structure of the receptacle.

Further, this receptacle has an outer wall formed of the first and second sheets having flexibility. Thus, when the receptacle is transferred or transported before use, the sheets may be folded or rolled up to take measures to provide a compact transport shape. In particular, many of conventional receptacles are formed to have a cylindrical or circular truncated cone shape. While these conventional receptacles have a certain degree of flexibility, they are designed to maintain the above shape, and thereby the flexibility is relatively low. Comparing with such conventional receptacles, this receptacle can have a drastically compactified transport shape.

Preferably, the receptacle comprises a first sheet having air-imperviousness and liquid-imperviousness, a second sheet having air-perviousness and liquid-imperviousness to serve as the air-pervious/liquid-impervious element and a peripheral edge joined to a peripheral edge of the first sheet, and a rigid port portion joined between the first and second sheets and adapted to form a part of a passage for introducing waste liquid between the first and second sheets, wherein the receptacle is designed to allow the first and second sheets to be entirely surrounded by the rigid case while air-tightly attaching an outer peripheral surface of the port portion to the rigid case.

According to this feature, the receptacle can have a more simplified structure formed by joining the first sheet having air-imperviousness and liquid-imperviousness, and the second sheet having air-perviousness and liquid-imperviousness together.

Further, this receptacle has an outer wall formed of the first and second sheets having flexibility. Thus, when the receptacle is transferred or transported before use, the sheets may be folded or rolled up to take measures to provide a compact transport shape. In particular, many of conventional receptacles are formed to have a cylindrical or circular truncated cone shape. While these conventional receptacles have a certain degree of flexibility, they are designed to maintain the above shape, and thereby the flexibility is relatively low. Comparing with such conventional receptacles, this receptacle can have a drastically compactified transport shape.

Preferably, the receptacle comprises a bag-shaped sheet having air-imperviousness and liquid-imperviousness and adapted to collect waste liquid in an interior space thereof, and a communication member for forming a passage which provides fluid communication between the interior and exterior spaces of the sheet, wherein the air-pervious/liquid-impervious element is incorporated in the communication member in such a manner as to close the passage.

According to this feature, the sheet and the communication member incorporating the air-pervious/liquid-impervious element can be formed as separated members. Thus, comparing with a sheet integrally formed with the air-pervious/liquid-impervious element, the above sheet can be formed at a lower cost.

Further, this receptacle has no need for integrally forming the air-pervious/liquid-impervious element in the sheet. This makes it possible to form the sheet using one appropriately selected from a plurality of materials suitable for being formed into a bag shape, so as to avoid restrictions on sheet production processes which would otherwise occur when the air-pervious/liquid-impervious element is integrally formed with a sheet.

Preferably, the above receptacle further includes a fastening element for fastening a folded portion of the sheet to prevent the folded portion from being unfolded. The fastening element may be designed to release the fastened state of the folded portion in response to expansion of the receptacle which is caused by a difference between a pressure in a space located inside the rigid case and outside the receptacle and a pressure in the interior space of the receptacle, occurring in an initial stage of the creation of a negative pressure in the interior space of the rigid case.

According to this feature, in the receptacle designed to collect waste liquid using the above sheet, the fastening element allows a folded portion of the receptacle to be maintained in a fastened state so as to provide a compact shape during packaging. In addition, the fastening element is designed to release the fastened state of the folded portion in response to the pressure difference. Thus, even if the receptacle is inserted into the interior space of the rigid case while maintaining the packaged shape, the receptacle can be returned to its original unfolded state in response to a negative pressure in the interior space of the rigid case.

Many of the conventional receptacles having a cylindrical or circular truncated cone shape are formed to have a flattened shape during packaging. In the use of such conventional receptacles, a medical staff is obliged to take certain action for reshaping, for example, extending the flattened receptacle, and then attaching the reshaped receptacle to the rigid case. In contrast, this receptacle can be attached to the rigid case while maintaining the packaged shape, to save medical staff's time and effort for setting up the receptacle.

Preferably, the receptacle further includes a coagulating agent adapted to coagulate the collected waste liquid.

According to this feature, the collected waste liquid can be coagulated. This makes it possible to prevent leakage of the waste liquid during transportation of the receptacle after completion of the waste-liquid collecting operation, and to subject the coagulated waste liquid to a treatment, such as incineration.

Preferably, the above receptacle further includes a partition portion for partitioning the interior space of the receptacle into a waste-liquid receiving chamber for collecting waste liquid therein and a coagulating-agent storage chamber for storing the coagulating agent. The partition portion may be adapted to provide fluid communication between the waste-liquid receiving chamber and the coagulating-agent storage chamber according to a given operation of a user.

According to this feature, the coagulating agent can be fed in the waste liquid according to need. Thus, it can be appropriately determined whether sucked waste liquid should be coagulated, depending on a volume of the waste liquid. For example, when the receptacle comprises a pair of sheets as described above, means for "providing fluid communication between the waste-liquid receiving chamber and the coagulating-agent storage chamber according to a given operation" may include a clamp member adapted to be detachably attached to the receptacle to clamp the sheets in such a manner as to divide the interior space of the receptacle into two chambers, and a weakly sealed portion formed between the sheets to releasably join the sheets together in such a manner as to divide the interior space of the receptacle into two chambers.

Also, there is provided a medical suction device comprising the above receptacle, a rigid case for detachably holding and air-tightly surrounding at least a portion of the receptacle, a suction-side tube fluidically connected between the rigid case and a suction source and adapted to create a negative-pressure atmosphere in an interior space of the rigid case, and a patient-side tube fluidically connected to the receptacle while maintaining the negative-pressure atmosphere in the interior space of the rigid case, and adapted to introduce waste liquid into the receptacle.

According to the medical suction device, a negative pressure is created in the interior space of the rigid case through the suction-side tube fluidically connected to the suction source, and a negative pressure is created in the interior space of the receptacle in response to the negative pressure in the interior space of the rigid case. Thus, the operation for sucking waste liquid can be initiated by attaching only the patient-side tube to the receptacle. This makes it possible to reduce a time period required for the preparatory operation and prevent an improper connection of tubes.

Further, in an operation for disposal of the collected waste liquid, the receptacle can be discarded together with the patient-side tube fluidically connected thereto simply after being detached from the rigid case. Thus, a time period required for the disposal operation can be reduced. This also makes it possible to reduce the frequency of contact of a medical staff with a component other than the receptacle and the patient-side tube to be discarded, during the disposal operation, so as to maximally prevent a secondary infection.

In the medical suction device, it is preferable that the rigid case has an upper end formed with an upward-facing opening for attaching and detaching the receptacle to/from the rigid case therethrough, and the suction-side tube has a regulator interposed therein and adapted to adjust a level of negative pressure to be created in the interior space of the rigid case. The regulator may be disposed under a bottom portion formed at a lower end of the rigid case.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. A receptacle for use with a medical suction device which is equipped with a rigid case for detachably holding and air-tightly surrounding at least a portion of said receptacle, and a patient-side tube for introducing waste liquid into said receptacle, and designed to create a negative pressure in both an interior space of said rigid case and an interior space of said receptacle so as to allow waste liquid to be sucked into said receptacle through said patient-side tube, said receptacle comprising:
   one port portion connected to said patient-side tube;
   a receptacle main body for holding waste fluid sucked through the port portion, said receptacle main body having a wall formed of sheets; and
   an air-pervious/liquid-impervious element having air perviousness and liquid imperviousness, said air-pervious/liquid-impervious element being provided in at least the portion of said receptacle main body, wherein
   said air-pervious/liquid-impervious element is adapted to discharge an air in the interior space of said receptacle to the interior space of said rigid case in response to the negative pressure created in the interior space of said rigid case,
   an outer peripheral portion of said port portion is detachably and air-tightly attachable to said rigid case, so that an entire region except for a part of said port portion is surrounded by said rigid case,
   said port portion includes a check valve adapted to allow waste liquid sucked from said patient-side tube to flow in, and prevents said waste liquid from flowing out to said patient-side tube, said receptacle main body has a folded portion that is located at a height position equal to or above said port portion in the state after said receptacle main body is held by said rigid case, and said folded portion being formed by folding sheets facing each other, and said air-previous/liquid-impervious element is located at a position below said port portion in the state after said receptacle main body is held by said rigid case, and a length of said receptacle main body in the state after said folded portion is expanded is set to be longer than said rigid case.

2. The receptacle as defined in claim 1, wherein said air-pervious/liquid-impervious element is located at a position corresponding to a liquid level for a target suction volume of waste liquid, in the state after being held by said rigid case.

3. The receptacle as defined in claim 2, wherein said air-pervious/liquid-impervious element is located over a given range below said liquid level for the target suction volume of waste liquid, in the state after being held by said rigid case.

4. The receptacle as defined in claim 1, wherein said receptacle main body includes:

a first sheet having air-imperviousness and liquid-imperviousness; and a second sheet including said air-pervious/liquid-impervious element and having a peripheral edge joined to a peripheral edge of said first sheet, and said port portion is rigid and joined between said first and second sheets and adapted to form a part of a passage for introducing waste liquid between said first and second sheets, and said receptacle is designed to allow said first and second sheets to be entirely surrounded by said rigid case while air-tightly attaching an outer peripheral surface of said port portion to said rigid case.

5. The receptacle as defined in claim 4, which further includes a fastening element for fastening a folded portion of said sheet to prevent said folded portion from being unfolded, said fastening element being designed to release the fastened state of said folded portion in response to expansion of said receptacle which is caused by a difference between a pressure in a space located inside said rigid case and outside said receptacle and a pressure in the interior space of said receptacle, occurring in an initial stage of the creation of a negative pressure in the interior space of said rigid case.

6. The receptacle as defined in claim 1, wherein said receptacle main body includes:

a bag-shaped sheet having air-imperviousness and liquid-imperviousness, said sheet being adapted to collect waste liquid in an interior space thereof; and a communication member for forming a passage which provides fluid communication between the interior and exterior spaces of said sheet, wherein said air-pervious/liquid-impervious element is incorporated in said communication member in such a manner as to close said passage.

7. The receptacle as defined in claim 1, which further includes a coagulating agent adapted to coagulate the collected waste liquid.

8. The receptacle as defined in claim 7, which further includes a partition portion for partitioning the interior space of said receptacle main body into a waste-liquid receiving chamber for collecting waste liquid therein and a coagulating-agent storage chamber for storing said coagulating agent, said partition portion being adapted to provide fluid communication between said waste-liquid receiving chamber and said coagulating-agent storage chamber according to a given operation of a user.

9. The receptacle as defined in claim 1, wherein the one port portion is the only port portion providing communication between the receptacle main body and areas external of the rigid case.

10. The receptacle as defined in claim 1, wherein the outer peripheral portion of said port portion is made of a synthetic resin having elasticity and being dimensioned to provide air-tightness with the rigid case.

11. The receptacle as defined in claim 1, wherein the port portion includes an internal portion disposed adjacent an internal surface of the rigid case, an external portion disposed adjacent an external surface of the rigid case, and a clamp portion between the internal and external portions of the port portion and configured for air tight engagement with areas of the rigid case between the internal and external surfaces thereof.

12. A receptacle for use with a medical suction device equipped with a rigid air-tight case having an interior space, the medical suction device being operative to create a negative pressure in the interior space, the receptacle further being for use with a patient-side tube external of the rigid case, the receptacle comprising:

a connection adaptor having a first end configured to be fluidically connected with the patient-side tube, a second end, a guide hole extending between the first and second ends and a clamped portion disposed between the first and second ends, the clamped portion having an outer peripheral surface configured for detachable air-tight connection with the rigid case so that the second end of the connection adaptor is disposed in the interior space; and a receptacle main body mounted to the second end of the connection adaptor and having an interior space communicating with the guide hole of the connection adaptor for holding waste fluid sucked through the patient-side tube and the guide hole, the receptacle main body having a wall formed of sheets and including an air-pervious/liquid-impervious element having air perviousness and liquid imperviousness, the air-pervious/liquid-imperviousness element being adapted to discharge air in the interior space of the receptacle to the interior space of the rigid case in response to the negative pressure created in the interior space of said rigid case, wherein said connection adaptor includes a check valve adapted to allow waste liquid sucked from said patient-side tube to flow in, and prevents said waste liquid from flowing out to said patient-side tube, said receptacle main body has a folded portion that is located at a height position equal to or above said connection adaptor in the state after said receptacle main body is held by said rigid case, and said folded portion being formed by folding sheets facing each other, and said air-pervious/liquid-impervious element is located at a position below said connection adaptor in the state after said receptacle main body is held by said rigid case, and a length of said receptacle main body in the state after said folded portion being expanded is set to be longer than said rigid case.

13. The receptacle as defined in claim 12, wherein the connection adaptor provides the only communication between the interior space of the receptacle main body and areas external of the rigid case.

14. The receptacle as defined in claim 13, wherein the clamped portion has an outer peripheral surface made of a synthetic resin having elasticity for providing the detachable air-tight connection between the connection adaptor and the rigid case.

\* \* \* \* \*